United States Patent [19]

Davalian et al.

[11] Patent Number: 5,616,719

[45] Date of Patent: Apr. 1, 1997

[54] PHOTOACTIVE INDICATOR COMPOUNDS

[75] Inventors: Dariush Davalian, San Jose; Rajendra Singh, Mountain View; Edwin F. Ullman, Atherton, all of Calif.

[73] Assignee: Behringwerke AG, Marburg, Germany

[21] Appl. No.: 438,154

[22] Filed: May 9, 1995

Related U.S. Application Data

[62] Division of Ser. No. 117,365, Sep. 3, 1993, abandoned.

[51] Int. Cl.[6] .................... C07D 213/90; C07D 311/02; C07C 255/00
[52] U.S. Cl. .................... 546/334; 549/285; 549/286; 549/400; 549/466; 549/479; 558/409; 548/228
[58] Field of Search ................... 549/286, 285, 549/400, 466, 479; 546/334; 548/228; 558/409

[56] References Cited

U.S. PATENT DOCUMENTS

| | | |
|---|---|---|
| 4,013,528 | 3/1977 | Chu et al. . |
| 4,233,402 | 11/1980 | Maggio et al. ............... 435/7 |
| 4,599,303 | 7/1986 | Yabusaki et al. ............. 435/6 |
| 4,650,770 | 3/1987 | Liu et al. ................... 436/523 |
| 4,683,195 | 7/1987 | Mullis et al. ................ 435/6 |
| 4,806,485 | 2/1989 | Birks et al. . |
| 4,822,733 | 4/1989 | Morrison et al. ............. 435/6 |
| 4,891,324 | 1/1990 | Pease et al. ................. 436/519 |
| 4,908,307 | 3/1990 | Rodland et al. .............. 435/6 |
| 5,019,496 | 5/1991 | Oster et al. ................. 435/6 |

*Primary Examiner*—Amelia Owens
*Attorney, Agent, or Firm*—Theodore J. Leitereg; Carol J. Roth

[57] ABSTRACT

Photoactive indicator compounds of the formula

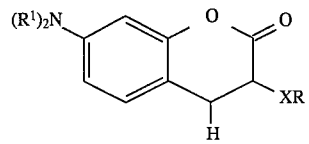

4 Claims, 1 Drawing Sheet

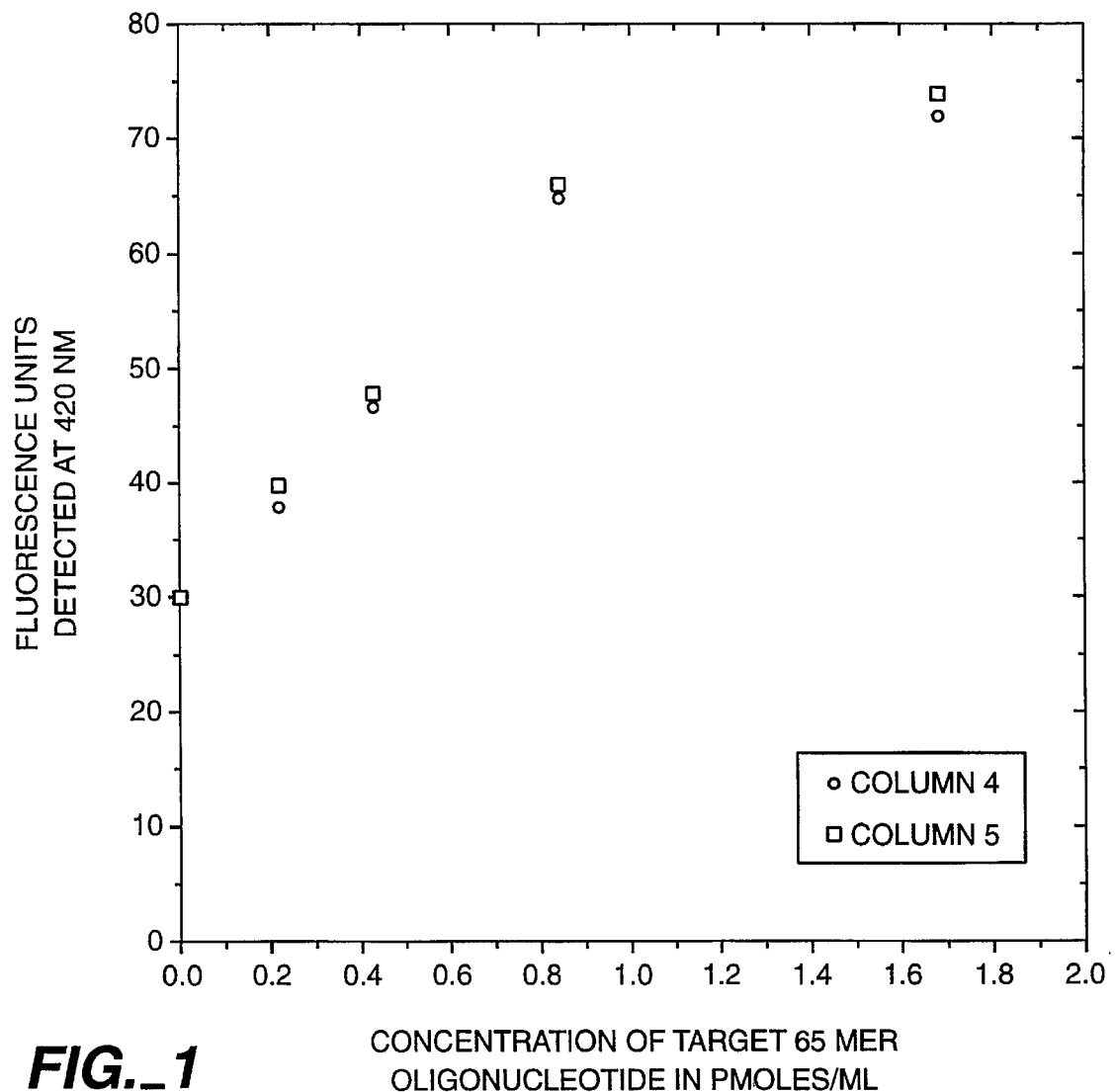
FIG._1

PHOTOACTIVE INDICATOR COMPOUNDS

This is a divisional of application Ser. No. 08/117,365, filed Sep. 3, 1993 now abandoned.

BACKGROUND OF THE INVENTION

Field of the Invention

This invention relates to methods, compositions and kits for determining an analyte in a sample. In particular, this invention relates to specific binding assays which utilize a photoactive indicator precursor which can react with singlet oxygen to form a fluorescent product.

The clinical diagnostic field has seen a broad expansion in recent years, both as to the variety of materials (analytes) that may be readily and accurately determined, as well as the methods for the determination. Convenient, reliable and non-hazardous means for detecting the presence of low concentrations of materials in liquids is desired. In clinical chemistry these materials may be present in body fluids in concentrations below $10^{-12}$ molar. The difficulty of detecting low concentrations of these materials is enhanced by the relatively small sample sizes that can be utilized.

In developing an assay there are many considerations. One consideration is the signal response to changes in the concentration of an analyte. A second consideration is the ease with which the protocol for the assay may be carried out. A third consideration is the variation in interference from sample to sample. Ease of preparation and purification of the reagents, availability of equipment, ease of automation and interaction with material of interest are some of the additional considerations in developing a useful assay.

One broad category of techniques involves the use of a receptor which can specifically bind to a particular spacial and polar organization of a labeled ligand as a function of the presence of an analyte. The observed effect of binding by the receptor will depend upon the label. In some instances the binding of the receptor merely provides for a differentiation in molecular weight between bound and unbound labeled ligand. In other instances the binding of the receptor will facilitate separation of bound labeled ligand from free labeled ligand or it may affect the nature of the signal obtained from the label so that the signal varies with the amount of receptor bound to labeled ligand. A further variation is that the receptor is labeled and the ligand unlabeled. Alternatively, both the receptor and ligand are labeled or different receptors are labeled with two different labels, whereupon the labels interact when in close proximity and the amount of ligand present affects the degree to which the labels of the receptor may interact.

There is a continuing need for new and accurate techniques that can be adapted for a wide spectrum of different ligands or be used in specific cases where other methods may not be readily adaptable.

Homogeneous immunoassays in which it is unnecessary to separate the bound and unbound label have previously been described for small molecules. These assays include SYVA's FRAT® assay, EMIT® assay, enzyme channeling immunoassay, and fluorescence energy transfer immunoassay (FETI); enzyme inhibitor immunoassays (Hoffmann LaRoche and Abbott Laboratories): fluorescence polarization immunoassay (Dandlicker), among others. All of these methods have limited sensitivity, and only a few including FETI and enzyme channeling, are suitable for large multi-epitopic analytes.

Hererogenous immunoassays in which a separation step is required are generally useful for both small and large molecules. Various labels have been used including enzymes (ELISA), fluorescent labels (FIA), radiolabels (RIA), chemiluminescent labels (CLA), etc.

Luminescent compounds, such as fluorescent compounds and chemiluminescent compounds, find wide application in the assay field because of their ability to emit light. For this reason, luminescers have been utilized as labels in assays such as nucleic acid assays and immunoassays. For example, a member of a specific binding pair is conjugated to a luminescer and various protocols are employed. The luminescer conjugate can be partitioned between a solid phase and a liquid phase in relation to the amount of analyte in a sample suspected of containing the analyte. By measuring the luminescence of either of the phases, one can relate the level of luminescence observed to a concentration of the analyte in the sample.

Particles, such as latex beads and liposomes, have also been utilized in assays. For example, in homogeneous assays an enzyme may be entrapped in the aqueous phase of a liposome labelled with an antibody or antigen. The liposomes are caused to release the enzyme in the presence of a sample and complement. Antibody- or antigen-labelled liposomes, having water soluble fluorescent or non-fluorescent dyes encapsulated within an aqueous phase or lipid soluble dyes dissolved in the lipid bilayer of the lipid vesicle, have also been utilized to assay for analytes capable of entering into an immunochemical reaction with the surface bound antibody or antigen. Detergents have been used to release the dyes from the aqueous phase of the liposomes. Particles have been dyed with fluorescent dyes and used as labels in immunoassays. Undyed particles have also been used (e.g., latex agglutination).

Related Art

European Published Patent Application No. 0 345 776 (McCapra) discloses specific binding assays that utilize a sensitizer as a label. The sensitizers include any moiety which, when stimulated by excitation with radiation of one or more wavelengths or other chemical or physical stimulus (e.g., electron transfer, electrolysis, electroluminescence or energy transfer) will achieve an excited state which (a) upon interaction with molecular oxygen will produce singlet molecular oxygen, or (b) upon interaction with a leuco dye will assume a reduced form that can be returned to its original unexcited state by interaction with molecular oxygen resulting in the production of hydrogen peroxide. Either interaction with the excited sensitizer will, with the addition of reagents, produce a detectible signal.

European Published Patent Application No. 0 476 556 (Motsenbocker) discloses a method for determination of a light sensitive substance wherein irradiation of lumigenic substance-light sensitive substance solution with modulated light is used to generate short wavelength light proportionally to the concentration of the light sensitive substance.

Luminescent labels for immunoassays are described in McCapra et al., *Journal of Bioluminescence and Chemiluminescence* (1989), Vol. 4, pp. 51–58.

European Published Patent Application No. 0 515 194 (Ullman et al.) discloses methods for determining an analyte in a medium suspected of containing the analyte. One such disclosed method comprises treating a medium suspected of containing an analyte under conditions such that the analyte, if present, causes a photosensitizer and a chemiluminescent compound to come into close proximity. The photosensitizer generates singlet oxygen and activates the chemiluminescent compound when it is in close proximity. The activated chemiluminescent subsequently produces light upon activation by singlet oxygen. The amount of light produced is related to the amount of analyte in the medium.

In this method, each singlet oxygen that is generated can react with no more than one chemiluminescent compound, which, in turn, can emit not more than one photon of light. The sensitivity of the method is therefore limited by the chemiluminescence quantum efficiency of the chemiluminescent compound, and, more importantly, by the ability to detect the limited number of photons that will be emitted upon reaction with singlet oxygen.

SUMMARY OF THE INVENTION

The present invention is directed to methods for determining an analyte, kits for conducting assays for an analyte, and compounds useful in the methods and assays.

One aspect of the invention is a method for determining an analyte which is an specific binding pair (sbp) member. In one embodiment of this aspect the method comprises a first step of providing in combination a medium suspected of containing an analyte; a photosensitizer capable in its excited state of generating singlet oxygen, wherein the photosensitizer is associated with a sbp member; and a photoactive indicator precursor capable of forming a photoactive indicator upon reaction with singlet oxygen, wherein the photoactive indicator precursor is associated with an sbp member; then a second step of exciting the photosensitizer by irradiation with light; and a final step of measuring the fluorescence of the photoactive indicator. At least one of the sbp members is capable of binding directly or indirectly to the analyte or to an sbp member complementary to the analyte. The fluorescence measured is related to the amount of the analyte in the medium.

In another embodiment, the method comprises the first step of combining in an aqueous medium a sample suspected of containing an analyte; a first suspendible particle comprised of a photosensitizer capable in its excited state of generating singlet oxygen, wherein the particle has a specific binding pair (sbp) member bound thereto; and a second suspendible particle comprised of a photoactive indicator precursor capable of forming a photoactive indicator upon reaction with singlet oxygen, wherein the particle has a sbp member bound thereto; a second step of irradiating the medium to excite the photosensitizer to generate singlet oxygen; and a final step of measuring the fluorescence of the photoactive indicator. Each sbp member is capable of binding directly or indirectly with the analyte or to an sbp member complementary to the analyte. The fluorescence measured is related to the amount of the analyte in the medium.

In another embodiment, the method comprises a first step of providing in combination a medium suspected of containing an analyte; a photosensitizer capable in its excited state of generating singlet oxygen, wherein the photosensitizer is associated with a sbp member; and a suspendible particle having bound thereto an sbp member, wherein the suspendible particle comprises a photoactive indicator precursor capable of forming a photoactive indicator upon reaction with singlet oxygen; a second step of irradiating the combination with light to excite the photosensitizer; and a final step of measuring the fluorescence of the photoactive indicator. Each sbp member is capable of binding directly or indirectly to the analyte or to a sbp member complementary to the analyte. The fluorescence measured is related to the amount of the analyte in the medium.

Another aspect of the invention is a method for determining an analyte. The method comprises a first step of providing in combination a medium suspected of containing an analyte; a photosensitizer capable in its excited state of generating singlet oxygen, wherein the photosensitizer is associated with a first specific binding pair (sbp) member; and a photoactive indicator precursor capable of forming a photoactive indicator upon reaction with singlet oxygen, wherein the photoactive indicator precursor is associated with a second sbp member; a second step of irradiating the combination with light to excite the photosensitizer; and a final step of measuring the fluorescence of the photoactive indicator. Each sbp member is capable of binding directly or indirectly to the analyte or to a sbp member complementary to the analyte. The fluorescence measured is related to the amount of the analyte in the medium.

Another aspect of this invention is a method for determining a polynucleotide analyte. The method comprises a first step of combining in an aqueous medium the analyte; one or more polynucleotide probes (wherein each probe contains a nucleotide sequence complementary to a nucleotide sequence of the analyte and wherein at least one probe is associated with a specific binding pair (sbp) member that is different from said complementary nucleotide sequence); a photosensitizer capable in its excited sate of generating singlet oxygen (wherein said photosensitizer is associated with a polynucleotide having a sequence complementary to a nucleotide sequence of said probe); and a photoactive indicator precursor capable of forming a photoactive indicator upon reaction with singlet oxygen, wherein the photoactive indicator precursor is associated with an sbp member complementary to the sbp member associated with the probe; a second step of irradiating the medium with light to excite the photosensitizer to generate singlet oxygen; and a third step of measuring the fluorescence of the photoactive indicator. The fluorescence is related to the amount of the analyte in the medium.

Another aspect of this invention is a composition comprising suspendible particles of average diameter of 20 to 4000 nanometers having associated therewith a photoactive indicator precursor, wherein the photoactive indicator precursor contains an selenium or tellurium atom.

Another aspect of this invention is a kit for conducting an assay for analyte. The kit comprises, in packaged combination, suspendible particles comprising a photoactive indicator precursor, wherein said photoactive indicator precursor contains a selenium or a tellurium atom and wherein the particles have bound thereto a sbp member; and a photosensitizer which is associated with a sbp member and is capable in its excited state of activating oxygen to its singlet state, wherein at least one of the sbp members is capable of binding to the analyte or to an sbp member complementary to the analyte.

In another embodiment of this aspect, the kit comprises, in packaged combination, a composition, which comprises a first suspendible particle comprising a photoactive indicator precursor containing a selenium or tellurium atom, wherein the first particle has bound thereto a sbp member; and a second suspendible particle comprising a photosensitizer, wherein the second particle has bound thereto a sbp member. At least one of the sbp members is capable of binding to the analyte or to an sbp member complementary to the analyte.

In another embodiment of this aspect, the kit comprises, in packaged combination, a photoactive indicator precursor containing a selenium or tellurium atom, wherein the photoactive indicator precursor is associated with a first sbp member; and a photosensitizer capable in its excited state of activating oxygen to its singlet state associated with a second sbp member. The sbp members are capable of binding to the analyte or to a sbp member capable of binding the analyte.

Another aspect of this invention is a binding assay for an analyte that is a sbp member. The assay comprises the first step of combining a medium suspected of containing the analyte with a sbp member capable of binding directly or indirectly to the analyte or to a sbp member complementary to the analyte; a second step of detecting the binding of the sbp member to the analyte or the complementary sbp member, wherein the detection comprises exposing a photoactive indicator precursor in the medium to singlet oxygen to produce a photoactive indicator; and a final step of measuring the fluorescence of the photoactive indicator.

Another aspect of this invention are compounds useful as photoactive indicator precursors which contain the following structure:

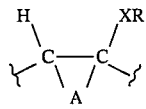 (I)

wherein H is cis to the XR group; X is a selenium or tellurium; R is an organic or organometallic group bound to X through an unsaturated carbon atom, a silicon atom, or a tin atom; and A, when taken with the carbon-carbon group, forms an alicyclic ring (optionally fused to one or more aromatic rings) or a heterocyclic ring; where upon reaction of the compound with singlet oxygen, the H and the XR group are replaced by a carbon-carbon double bond to yield a fluorescent molecule having an extinction coefficient of at least 10,000 $M^{-1}cm^{-1}$ at its absorption maximum and a fluorescence emission quantum yield of at least 0.1.

Another aspect of this invention is a method for preparing a photoactive indicator molecule. The method comprises reacting a compound of the invention (as described above) with singlet oxygen to yield a photoactive indicator having an extinction coefficient of at least 10,000 $M^{-1}cm^{-1}$ at its absorption maximum and a fluorescence emission quantum yield of at least 0.1.

One of the advantages of the present invention is the ability of the fluorescent photoactive indicator (which is produced from the reaction of the photoactive indicator precursor with singlet oxygen) to generate at least $10^{-5}$ times as many photons as the chemiluminescent compound used in the method described above in European Published Patent Application No. 0 515 194. This is because a single fluorescent photoactive indicator molecule can often be excited up to $10^{-5}$ times before it is destroyed. Thus, the fluorescent photoactive indicator molecule that is formed in the present invention can produce tens of thousands of photons on irradiation. Detection of this fluorescence can therefore provide a more sensitive assay. Moreover, measurement of the fluorescence of the photoactive indicator molecule in the present invention permits the use of a standard fluorometer whereas detection of the chemiluminescence produced on activation of the chemiluminescent compound in the previously described assay requires more specialized spectrometers.

BRIEF DESCRIPTION OF THE DRAWINGS

FIG. 1 is a graphic depiction of the results of DNA detection assays. The results of each assay are depicted by a different symbol.

DETAILED DESCRIPTION OF THE INVENTION

Definitions

As used in this specification and appended claims, unless specified to the contrary, the following terms have the meaning indicated:

"Alkyl" refers to a monovalent branched or unbranched radical derived from an aliphatic hydrocarbon by removal of one hydrogen atom; includes both lower alkyl and upper alkyl.

"Lower alkyl" refers to an alkyl radical containing from 1 to 5 carbon atoms, e.g., methyl, ethyl, propyl, butyl, isopropyl, isobutyl, pentyl, isopentyl, and the like.

"Upper alkyl" refers to an alkyl radical containing more than 6 carbon atoms, usually 6 to 20 carbon atoms, e.g., hexyl, heptyl, octyl, and the like.

"Alkylidene" refers to a divalent organic radical derived from an alkyl radical in which two hydrogen atoms are taken from the same carbon atom, e.g., ethylidene, and the like.

"Alkylene" refers to a divalent organic radical derived from an alkyl radical in which two hydrogen atoms are taken from different carbon atoms.

"Alicyclic ring" refers to a cyclic hydrocarbon radical of 5 to 7 carbons in length which may be unsaturated or partially saturated.

"Aryl" refers to an organic radical derived from an aromatic hydrocarbon by the removal of one atom and containing one or more aromatic rings, usually one to four aromatic rings, e.g., phenyl (from benzene), naphthyl (from naphthalene), and the like.

"Aralkyl" refers to an organic radical having an alkyl group to which is attached an aryl group, e.g., benzyl, phenethyl, 3-phenylpropyl, 1-naphthylethyl, and the like.

"Alkoxy" refers to a radical of the formula —$OR_a$ where $R_a$ is an alkyl group, e.g., methoxy, ethoxy, and the like.

"Aryloxy" refers to a radical of the formula —$OR_b$ where $R_b$ is an aryl group, e.g., phenoxy, naphthoxy, and the like.

"Aralkoxy" refers to a radical of the formula —$OR_c$ where $R_c$ is an aralkyl radical, e.g., benzyloxy, 1-naphthylethoxy, and the like.

"Alkylthio" refers to a radical of the formula —$SR_a$ where $R_a$ is an alkyl group, e.g., methylthio, ethylthio, and the like.

"Arylthio" refers to a radical of the formula —$SR_b$ where $R_b$ is an aryl group, e.g., phenylthio, naphthylthio, and the like.

"Heterocyclic ring" refers to a stable mono-, bi- or tricyclic ring system which consists of carbon atoms and from one to three heteroatoms selected from the group consisting of nitrogen, oxygen and sulfur and which is either saturated or unsaturated, wherein the nitrogen, carbon or sulfur atoms may optionally be oxidized, and the nitrogen atom may optionally be quaternized, and includes any ring system in which any of the above-defined heterocyclic ring systems is fused to a benzene ring. The heterocyclic ring system may be substituted at any heteroatom or carbon atom which results in the creation of a stable structure. Examples of such heterocyclic ring systems include, but are not limited to, piperidine, piperazine, 2-oxopiperazine, 2-oxopiperidine, 2-oxopyrrolidine, 2-oxoazepine, azepine, pyrrole, 4-piperidone, pyrrolidine, pyrazole, pyrazolidine, imidazole, imidazoline, imidazolidine, pyridine, pyrazine, pyrimidine, pyridazine, oxazole, oxazolidine, indane, isoxazole, isoxazolidine, morpholine, thiazole, thiazolidine, isothiazole, quinuclidine, isothiazolidine, indole, isoindole, indoline, isoindoline, octahydroindole, octahydroisoindole, quinoline, isoquinoline, decahydroisoquinoline, benzimidazole, thiadiazole, dihydrobenzofuran, benzofuran, benzopyran, 1,4-benzopyrone, 1,2-benzopyrone, benzothiazole, benzoxazole, furan, tetrahydrofuran, pyran, tetrahydropyran, thiophene, benzothiophene, thiamorpholine, thiamorpholine sulfoxide, thiamorpholine sulfone, and oxadiazole. Preferred heterocyclic rings for the purposes of this invention are benzopyrones.

"Substituted" refers to the condition wherein a hydrogen atom of a molecule has been replaced by another atom, which may be a single atom such as a halogen, etc., or part of a group of atoms, such as an organic group.

"Electron-donating group" refers to a substituent which, when bound to a molecule, is capable of polarizing the molecule such that the electron-donating group becomes electron poor and positively harged relative to another portion of the molecule, i.e., has reduced electron density. Such groups may be, by way of illustration and not limitation, amines, ethers, thioethers, phosphines, hydroxy, oxyanions, mercaptans and their anions, sulfides, etc.

"Organic group" refers to a substituent having from 1 to 50 atoms other than the requisite number of hydrogen atoms necessary to satisfy the valencies of the atoms in the radical. Generally, the predominant atom in such a group is carbon (C) but may also be oxygen (O), nitrogen (N), sulfur (S), phosphorus (P), wherein, if present, the O, N, S, or P atom may be bound to carbon or to one or more of each other or to hydrogen or to a metal atom to form various functional groups, such as carboxylic acids, alcohols, thiols, carboxamides, carbamates, carboxylic acid esters, sulfonic acids, sulfonic acid esters, phosphoric acids, phosphoric acid esters, ureas, carbamates, phosphoramides, sulfonamides, ethers, sulfides, thioethers, olefins, acetylenes, amines, ketones, aldehydes, nitriles, and the like. Illustrative of such organic groups, by way of illustration and not limitation, are alkyl, alkylidine, aryl, aralkyl, and heterocyclyl, wherein the alkyl, alkylidine, aryl, aralkyl or heterocyclyl group may be substituted with one or more of the aforementioned functional groups.

"Organometallic group" refers to a radical containing an organic group (as defined above) linked to a metal atom.

"Analyte" refers to the compound or composition to be detected. The analyte can be comprised of a member of a specific binding pair (sbp) and may be a ligand, which is monovalent (monoepitopic) or polyvalent (polyepitopic), usually antigenic or haptenic, and is a single compound or plurality of compounds which share at least one common epitopic or determinant site. The analyte can be a part of a cell such as bacteria or a cell bearing a blood group antiget such as A, B, D, etc., or an HLA antigen or a microorganism, e.g., bacterium, fungus, protozoan, or virus.

The polyvalent ligand analytes will normally be poly(amino acids), i.e., polypeptides and proteins, polysaccharides, nucleic acids, and combinations thereof. Such combinations include components of bacteria, viruses, chromosomes, genes, mitochondria, nuclei, cell membranes and the like.

For the most part, the polyepitopic ligand analytes to which the subject invention can be applied will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

A wide variety of proteins may be considered as to the family of proteins having similar structural features, proteins having particular biological functions, proteins related to specific microorganisms, particularly disease causing microorganisms, etc. Such proteins include, for example, immunoglobulins, cytokines, enzymes, hormones, cancer antigens, nutritional markers, tissue specific antigens, etc.

The types of proteins, blood clotting factors, protein hormones, antigenic polysaccharides, microorganisms and other pathogens of interest in the present invention are specifically disclosed in U.S. Pat. No. 4,650,770, the disclosure of which is incorporated by reference herein in its entirety.

The monoepitopic ligand analytes will generally be from about 100 to 2,000 molecular weight, more usually from 125 to 1,000 molecular weight.

The analytes include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which include cocaine and benzyl ecgonine, their derivatives and metabolites; ergot alkaloids, which include the diethylamide of lysergic acid; steroid alkaloids; iminazoyl alkaloids; quinazoline alkaloids; isoquinoline alkaloids; quinoline alkaloids, which include quinine and quinidine; diterpene alkaloids, their derivatives and metabolites.

The next group of drugs includes steroids, which includes the estrogens, androgens, andreocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

The next group of drugs is lactams having from 5 to 6 annular members, which include the barbiturates, e.g., phenobarbital and secobarbital, diphenylhydantoin, primidone, ethosuximide, and their metabolites.

The next group of drugs is aminoalkylbenzenes, with alkyl of from 2 to 3 carbon atoms, which includes the amphetamines; catecholamines, which includes ephedrine, L-dopa, epinephrine; narceine; papaverine; and metabolites of the above.

The next group of drugs is benzheterocyclics which include oxazepam, chlorpromazine, tegretol, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs is the hormones such as thyroxine, cortisol, triiodothyronine, testosterone, estradiol, estrone, progesterone, polypeptides such as angiotensin, LHRH, and immunosuppressants such as cyclosporin, FK506, mycophenolic acid, and so forth.

The next group of drugs includes the vitamins such as A, B (e.g., $B_{12}$), C, D, E and K, folic acid, thiamine.

The next group of drugs is prostaglandins, which differ by the degree and sites of hydroxylation and unsaturation.

The next group of drugs is the tricyclic antidepressants, which include imipramine, dismethylimipramine, amitriptyline, nortriptyline, protriptyline, trimipramine, chlomipramine, doxepine, and desmethyldoxepin, The next group of drugs are the anti-neoplastics, which include methotrexate.

The next group of drugs is antibiotics, which include penicillin, chloromycetin, actinomycetin, tetracycline, terramycin, the metabolites and derivatives.

The next group of drugs is the nucleosides and nucleotides, which include ATP, AND, FMN, adenosine, guanosine, thymidine, and cytidine with their appropriate sugar and phosphate substituents.

The next group of drugs is miscellaneous individual drugs which include methadone, meprobamate, serotonin, meperidine, lidocaine, procainamide, acetylprocainamide, propranolol, griseofulvin, valproic acid, butyrophenones, antihistamines, chloramphenicol, anticholinergic drugs, such as atropine, their metabolites and derivatives.

Metabolites related to diseased states include spermine, galactose, phenylpyruvic acid, and porphyrin Type 1.

The next group of drugs is aminoglycosides, such as gentamicin, kanamycin, tobramycin, and amikacin.

Among pesticides of interest are polyhalogenated biphenyls, phosphate esters, thiophosphates, carbamates, polyhalogenated sullenamides, their metabolites and derivatives.

For receptor analytes, the molecular weights will generally range from 10,000 to $2\times10^8$, more usually from 10 000 to $10^6$. For immunoglobulins, IgA, IgG, IgE and IgM, the molecular weights will generally vary from about 160,000 to about $10^6$. Enzymes will normally range from about 10,000 to 1,000,000 in molecular weight. Natural receptors vary widely, generally being at least about 25,000 molecular weight and may be $10^6$ or higher molecular weight, including such materials as avidin, streptavidin, DNA, RNA, thyroxine binding globulin, thyroxine binding prealbmin, transcortin, etc.

The term analyte further includes polynucleotide analytes such as those polynucleotides defined below. These include m-RNA, r-RNA, t-RNA, DNA, DNA-ENA duplexes, etc. The term analyte also includes receptors that are polynucleotide binding agents, such as, for example, restriction enzymes, activators, repressors, nucleases, polymerases, histones, repair enzymes, chemotherapeutic agents, and the like.

The analyte may be a molecule found directly in a sample such as a body fluid from a host. The sample can be examined directly or may be pretreated to render the analyte more readily detectable. Furthermore, the analyte of interest may be determined by detecting an agent probative of the analyte of interest such as a specific binding pair member complementary to the analyte of interest, whose presence will be detected only when the analyte of interest is present in a sample. Thus, the agent probative of the analyte becomes the analyte that is detected in an assay. The body fluid can be, for example, urine, blood, plasma, serum, saliva, semen, stool, sputum, cerebral spinal fluid, tears, mucus, and the like.

"Specific binding pair (sbp) member" refers to one of two different molecules, having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs such as biotin-avidin, hormones-hormone receptors, nucleic acid duplexes, IgG-protein A, polynucleotide pairs such as DNA-DNA, DNA-RNA, and the like are not immunological pairs but are included in the invention and the definition of sbp member.

"Polynucleotide" refers to a compound or composition which is a polymeric nucleotide having in the natural state about 6 to 500,000 or more nucleotides and having in the isolated state about 6 to 50,000 or more nucleotides, usually about 6 to 20,000 nucleotides, more frequently 6 to 10,000 nucleotides. The term "polynucleotide" also includes oligonucleotides and nucleic acids from any source in purified or unpurified form, naturally occurring or synthetically produced, including DNA (dsDNA and ssDNA) and RNA, usually DNA, and may be t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof, and the like.

"Polynucleotide probe" refers to single-stranded nucleic acid molecules having base sequences complementary to that of the target polynucleotide analyte. Probes will generally consist of chemically or synthesized DNA or RNA polynucleotides from 6 to 200 base pair in length and must be capable of forming a stable hybridization complex with the target polynucleotide analyte.

"Ligand" refers to any organic compound for which a receptor naturally exists or can be prepared. The term ligand also includes ligand analogs, which are modified ligands, usually an organic radical or analyte analog, usually of a molecular weight greater than 100, which can compete with the analogous ligand for a receptor, the modification providing means to join the ligand analog to another molecule. The ligand analog will usually differ from the ligand by more than replacement of a hydrogen with a bond which links the ligand analog to a hub or label, but need not. The ligand analog can bind to the receptor in a manner similar to the ligand. The analog could be, for example, an antibody directed against the idiotype of an antibody to the ligand.

"Receptor" or "antiligand" refers to any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, avidin, protein A, barstar, complement component Clq, and the like. Avidin is intended to include egg white avidin and biotin binding proteins from other sources, such as streptavidin.

"Specific binding" refers to the specific recognition of one of two different molecules for the other compared to substantially less recognition of other molecules. Generally, the molecules have areas on their surfaces or in cavities giving rise to specific recognition between the two molecules. Exemplary of specific binding are antibody-antigen interactions, enzyme-substrate interactions, polynucleotide interactions, and so forth.

"Non-specific binding" refers to the non-covalent binding between molecules that is relatively independent of specific surface structures. Non-specific binding may result from several factors including hydrophobic interactions between molecules.

"Antibody" refers to an immunoglobulin which specifically binds to and is thereby defined as complementary with a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fraent thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, Fab', and the like. In addition, aggregates, polymers, and conjugates of immunoglobulins or their fragments can be used where appropriate so long as binding affinity for a particular molecule is maintained.

"Linking group" refers to the covalent linkage between molecules. The linking group will vary depending upon the nature of the molecules, such as a photosensitizer, a photoactive indicator precursor, a sbp member or the molecule associated with or part of a particle, being linked. Functional groups that are normally present or are introduced on a photosensitizer or a photoactive indicator precursor will be employed for linking these molecules to an sbp member or to a particle such as a lipophilic component of a liposome or oil droplet, latex particle, silicon particle, metal sol, or dye crystallite.

For the most part, carbonyl functionalities are useful as linking groups, such as oxocarbonyl groups such as aldehydes, acetyl and carboxy groups; and non-oxocarbonyl groups (including nitrogen and sulfur analogs) such as amidine, amidate, thiocarboxy and thionocarboxy. Alternative functionalities of oxo are also useful as linking groups, such as halogen, diazo, mercapto, olefin (particularly activated olefin), amino, phosphoro and the like. A good description of linking groups may be found in U.S. Pat. No. 3,817,837, which disclosure is incorporated herein by reference.

The linking groups may vary from a bond to a chain of from 1 to 100 atoms, usually from about 1 to 70 atoms, preferably 1 to 50 atoms, more preferably 1 to 20 atoms, each independently selected from the group normally consisting of carbon, oxygen, sulfur, nitrogen and phosphorous. The number of heteroatoms in the linking groups will normally range from about 0 to 20, usually from about 1 to 15, more preferably 2 to 6. The atoms in the chain may be substituted with atoms other than hydrogen in a manner similar to that described for organic groups. As a general rule, the length of a particular linking group can be selected arbitrarily to provide for convenience of synthesis, minimize interference of binding sbp members, and permit the incorporation of any desired group such as a fluorescent energy acceptor, or a catalyst of intersystem crossing such as a heavy atom, and the like. The linking groups may be aliphatic or aromatic, although with diazo groups, aromatic groups will usually be involved.

When heteroatoms are present, oxygen will normally be present as oxo or oxy, bonded to carbon, sulfur, nitrogen or phosphorous; nitrogen will normally be present as nitro, nitroso or amino, normally bonded to carbon, oxygen, sulfur or phosphorous; sulfur would be analogous to oxygen; while phosphorous will be bonded to carbon, sulfur, oxygen or nitrogen, usually as phosphonate and phosphate mono- or diester.

Common functionalities in forming a covalent bond between the linking group and the molecule to be conjugated are alkylamine, amidine, thioamide, ether, urea, thiourea, guanidine, azo, thioether and carboxylate, sulfonate, and phosphate esters, amides and thioesters.

For the most part, where the photosensitizer and the photoactive indicator precursor of the present invention are linked to a particle, surface or sbp member, they will have a non-oxocarbonyl group (including nitrogen and sulfur analogs), a phosphate group, an amino group, an alkylating agent (e.g., such as halo or tosylalkyl), an ether group (including hydroxy), a thioether group (including mercapto), an oxocarbonyl group (e.g., aldehyde or ketone), or an active olefin such as a vinyl sulfone or an α,β-unsaturated ester or amide. These functionalities will be linked to a particle, surface or a sbp member having functionalities such as amine groups, carboxyl groups, active olefins, or alkylating agents, e.g., bromoacetyl. Where an amine and carboxylic acid or its nitrogen derivative or phosphoric acid are linked, amides, amidines and phosphoramides will be formed. Where mercaptan and activated olefin are linked, thioethers will be formed. Where a mercaptan and an alkylating agent are linked, thioethers will be formed. Where aldehyde and an amine are linked under reducing conditions, an alkylamine will be formed. Where a carboxylic acid or phosphate acid and an alcohol are linked, esters will be formed.

"A group or functionality imparting hydrophilicity or water solubility" refers to a hydrophilic functionality, which increases wettability of solids with water and the solubility in water of compounds to which it is bound. Such a functional group or functionality can be an organic group and can include a sulfonate, sulfate, phosphate, amidine, phosphonate, carboxylate, hydroxyl particularly polyols, amine, ether, amide, and the like. Illustrative functional groups are carboxyalkyl, sulfonoxyalkyl, CONHOCH$_2$COOH, CO-(glucosamine), sugars, dextran, cyclodextrin, SO$_2$NHCH$_2$COOH, SO$_3$H, CONHCH$_2$CH$_2$SO$_3$H, PO$_3$H$_2$, OPO$_3$H$_2$, hydroxyl, carboxyl, ketone, and combinations thereof. Most of the above functionalities can also be utilized as attaching groups, which permit attachment of the photosensitizer or photoactive indicator precursor to an sbp member or a support.

"A group or functionality imparting lipophilicity or lipid solubility" is a lipophilic functionality, which decreases the wettability of surfaces by water and the solubility in water of compounds to which it is bound. Such a functional group or functionality can contain 1 to 50 or more atoms, usually carbon atoms substituted with hydrogen or halogen and can include alkyl, alkylidene, aryl and aralkyl. The lipophilic group or functionality will normally have one to six straight or branched chain aliphatic groups of at least 6 carbon atoms, more usually at least 10 carbon atoms, and preferably at least 12 carbon atoms, usually not more than 30 carbon atoms. The aliphatic group may be bonded to rings of from 5 to 6 members, which may be alicyclic, heterocyclic, or aromatic.

"Photosensitizer" refers to a molecule which, for the purposes of this invention, can be excited to a metastable state, usually a triplet state, which in the proximity of molecular oxygen can directly or indirectly transfer its energy to the oxygen with concomitant excitation of the oxygen to a highly reactive excited state of oxygen often referred to as singlet oxygen or $^1O_2$ ($^1\Delta_g$). The photosensitizer will usually be excited by the absorption of light or by an energy transfer from an excited state of a suitable donor but may also be excited by chemiexcitation, electrochemical activation or by other means. Usually excitation of the photosensitizer will be caused by irradiation with light from an external source. The photosensitizers of this invention will usually have an absorption maximum in the wavelength range of 250–1100 nm, preferably 300–1000 nm, and more preferably 450–950 nm, with an extinction coefficient at its absorbance maximum greater than 500 M$^{-1}$cm$^{-1}$, preferably at least 5000 M$^{-1}$cm$^{-1}$, more preferably at least 50,000 M$^{-1}$cm$^{-1}$. The lifetime of the excited state, usually a triplet state, produced following absorption of light by the photosensitizer will usually be at least 100 nsec, preferably at least 1 μsec in the absence of oxygen. In general, the lifetime must be sufficiently long to permit the energy transfer to oxygen, which will normally be present at concentrations in the range of $10^{-5}$ to $10^{-3}$M (depending on the medium). The excited state of the photosensitizer will usually have a different spin quantum number (S) than its ground state and will usually be in a triplet (S=1) state when, as is usually the case, the ground state is a singlet (S=0). Preferably, the photosensitizer will have a high intersystem crossing yield. That is, excitation of a photosensitizer will produce the long lived state (usually triplet) with an efficiency of at least 10%, desirably at least 40%, preferably greater than 80%. The photosensitizer will usually be at most weakly fluorescent under the assay conditions (quantum yield usually less than 0.5, preferably less that 0.1).

Photosensitizers of the instant invention are relatively photostable and will not react efficiently with the singlet molecular oxygen so generated. Several structural features are present in most useful photosensitizers. Most photosensitizers have at least one and frequently three or more conjugated double or triple bonds held in a rigid, frequently aromatic structure. They will frequently contain at least one group that accelerates intereystem crossing such as a carbonyl or imine group or a heavy atom selected from rows 3–6 of the periodic table, especially iodine or bromine, or they will frequently have polyaromatic structures. Typical photosensitizers include ketones such as acetone, benzophenone and 9-thioxanthone; xanthenes such as eosin and rose bengal; polyaromatic compounds such as buckminsterfullerene and 9,10-dibromoanthracene; porphyrins including metallo-porphyrins such as hematoporphyrin and chlorophylis; oxazines; cyanines; squarate dyes; phthalocyanines; merocyanines; thiazines such as methylene blue, etc., and derivatives of these compounds substituted by an organic group for enhancing intersystem crossing and rendering such compounds more lipophilic or more hydrophilic and/or as attaching groups for attachment, for example, to an sbp member. Examples of other photosensitizers that may be utilized in the present invention are those that have the above properties and are enumerated in N. J. Turro, "Molecular Photochemistry", page 132, W. A. Benjamin Inc., N.Y. 1965.

The photosensitizers of the instant invention are preferably relatively non-polar to assure dissolution into a lipophilic member when the photosensitizer is incorporated into a suspendible particle such as an oil droplet, liposome, latex particle, and the like.

"Photoactive indicator precursor" refers to those molecules which react with singlet oxygen to form photoactive indicators or to form a compound that can react with an auxiliary compound that is thereupon converted to a photoactive indicator. There are several types of reactions of singlet otgen that can give compounds that will lead to a photoactive indicator compound. The type of reaction that is employed and the choice of the photoactive indicator that is desired provides a guide to the structures of the photoactive indicator precursors and any auxiliary compounds used in the present invention.

The photoactive indicator precursor will preferably undergo a reaction with singlet oxygen that is very rapid, usually at least $10^4$–$10^6$ sec$^{-1}$, preferably at least $10^6$–$10^8$ sec$^{-1}$, more preferably $>10^8$ sec$^{-1}$. When the initial product of the reaction is an intermediate that reacts to give the photoactive precursor, the intermediate will preferably have a lifetime that is short relative to the desired time between forming singlet oxygen and detecting the fluorescence emitted from the photoactive indicator upon exposure to light. For simultaneous singlet oxygen generation and fluorescence detection the lifetime will usually be $10^{-3}$–10 sec, preferably $10^{-3}$ sec. When generation of singlet oxygen and fluorescence detection are sequential the lifetime may vary from $10^{-3}$ sec to 30 minutes or more, preferably <1 sec–60 sec.

Higher rates of reaction of singlet oxygen are achieved by providing singlet oxygen reactive groups in the photoactive indicator precursor that are electron rich. These groups will usually be an olefin or acetylene, hydrazine and hydroxylamine deroivatives, selenides and tellurides but are not limited to these groups. For example, tellurides have been found to be particularly useful because they react rapidly with singlet oxygen to produce an olefin. The reaction rate depends on the electron availability (oxidation potential) of the tellurium. For example, electron donating groups on an aryl ring substituent on the tellurium atom can increase the rate. Changing from tellurium to selenium (the next lower chalcogenide) will decrease the rate, but increase the oxidation stability of the molecule.

When the photoactive indicator precursor contains a hydrazine or hydrazide, reaction with singlet oxygen can produce a double bond. For example, singlet oxygen can convert hydrazides directly into fluorescent photoactive indicators, as illustrated in the following reaction:

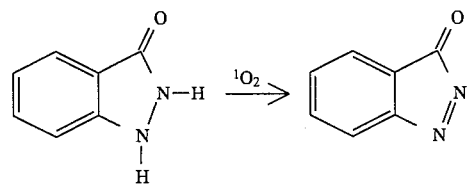

The oxidation potential of a hydrazine is an important factor in providing a high rate of reaction. Electron withdrawing groups such as an acyl group (e.g., as in a hydrazide) slow the reaction although acyl hydrazides and diacyl hydrazides can still be used as photoactive indicator precursors in the present invention. When the reaction is insufficiently rapid it can often be accelerated in the presence of a base. For example, 3-aminophthaloyl hydrazide forms an anion in the presence of strong base that is electron rich and can react rapidly with singlet oxygen to form 3-aminophthalate as the photoactive indicator. However, the hydroxyl ion cannot be used as a base when the suspendible particles contain the photoactive indicator precursor within a hydrophobic matrix. Hydrophilic particles such as agarose can be used instead to permit access to the hydroxyl ion. Usually the photoactive indicator precursor will be covalently bound to the suspendible particle when the particle is hydrophilic.

Still another example of a useful singlet oxygen reaction is the reaction with electron rich olefins such as those described in European Published Patent Application No. 0 515 194. Two fundamental types of reactions are described. One of these is the "ene" reaction which is exemplified by the following transformation:

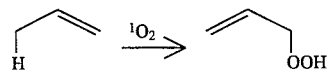

This reaction shifts the position of a double bond and produces a hydroperoxide. The double bond shift can cause two auxochromic groups in the photoactive indicator precursor to come into conjugation and thus produce a fluorescent photoactive indicator.

Other photoactive indicator precursors react with singlet oxygen to form hydroperoxides which can react internally with an oxidizable group to give a fluorescent photoactive indicator. An example of such a precursor and the subsequent reaction and product include the following:

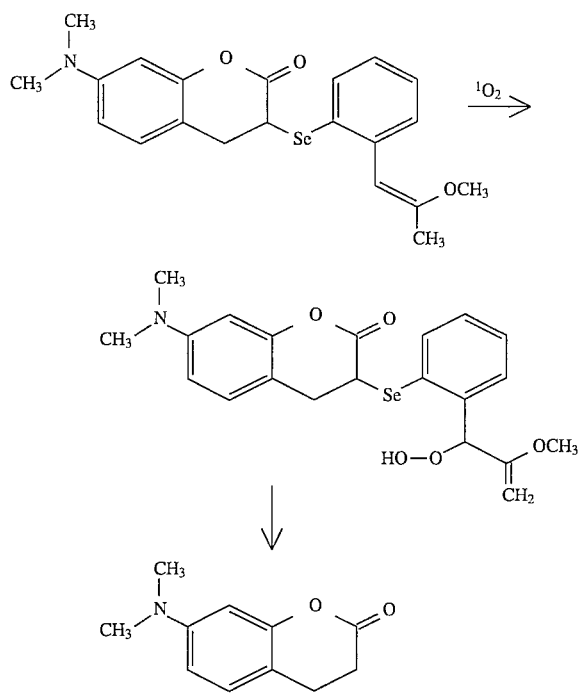

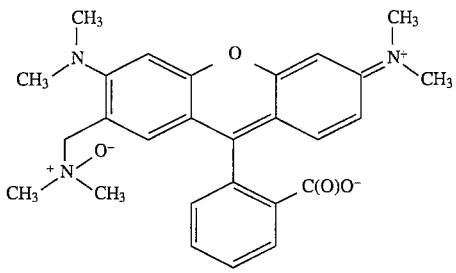

which is poorly fluorescent, can be oxygenated by a hydroperoxide to give the more highly fluorescent compound:

The auxiliary compound could alternatively have a selenium or tellurium atom that could react with a hydroperoxide to produce an intermediate that could undergo subsequent elimination to form a fluorescent photoactive indicator.

Alternatively, a hydroperoxide formed by reaction of singlet oxygen with a photoactive indicator precursor, such as 1,3-diphenylpropene, can serve to oxidize the leuco form of a dye which is present as an auxiliary compound so as to form a fluorescent photoactive indicator. The hydroperoxide can also oxygenate a group V element in an auxiliary compound to cause it to act as an electron donating quencher of an associated fluorescent group. For example, the auxiliary compound:

Alternatively, the photoactive indicator precursor will react slowly or not at all with singlet oxygen but will react with a hydroperoxide reaction product of singlet oxygen and an auxiliary molecule. For example, in the following reaction, the auxiliary compound is reacted with singlet oxygen to form a hydroperoxide, which is then reacted with the photoactive indicator precursor of formula (Ik) to form a fluorescent photoactive indicator:

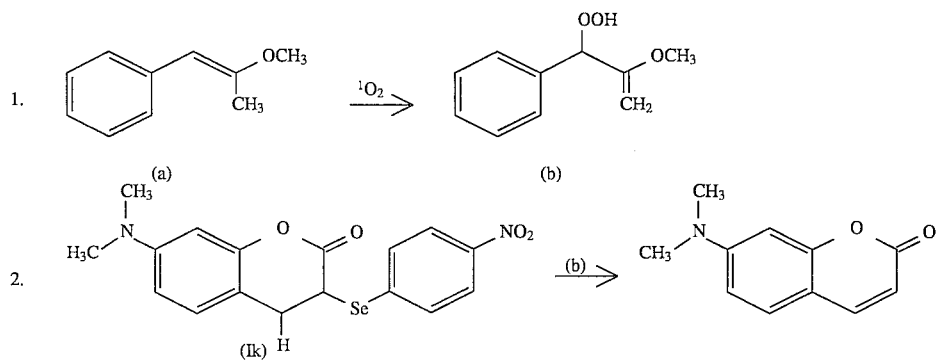

In each of these examples the auxiliary compound and the photoactive indicator precursor may be covalently linked. In such an occurrence, the resulting molecule is referred to as photoactive indicator precursor.

The second typical reaction of olefins with singlet oxygen is 2+2 addition to form a dioxetane. This reaction can lead to bond breaking and therefore can separate a quenching group from a fundamentally fluorescent molecule. Alternatively the bond breaking step can lead to a ketone, aldehyde or ester which could be fluorescent or which could undergo subsequent reactions that could lead to a fluorescent molecule.

In all of the above olefin reactions the rate will be faster if the olefin is substituted with electron donating groups such as ethers, thioethers, amines, and the like.

Still another type of reaction of singlet oxygen is 4+2 cycloadditions with dienes. Such reactions lead initially to endoperoxides. In some cases endoperoxides can rearrange to active esters or anhydrides that are capable of reaction with a suitably placed group to provide a lactone or lactam that can be fluorescent. For example, the endoperoxide formed in the following reaction scheme can rearrange to form a fluorescent lactone:

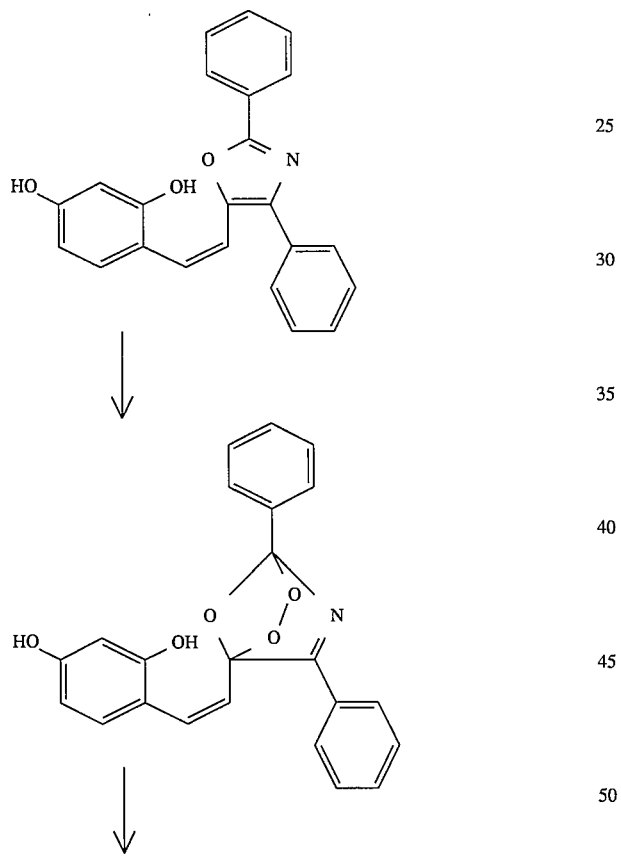

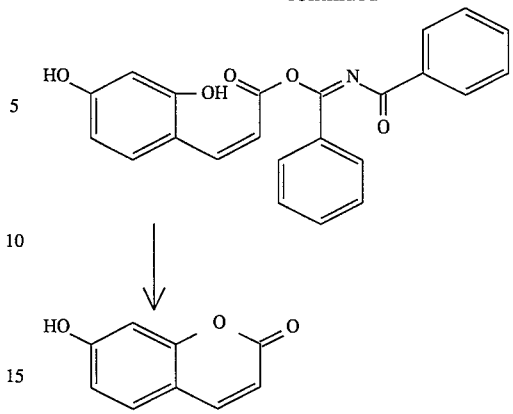

Alternatively, the endoperoxides may oxidize a photoactive indicator precursor much as described above for hydroperoxides.

Additional examples of photoactive indicator precursors' reaction with singlet oxygen to produce fluorescent photoactive indicator molecules are illustrated below:

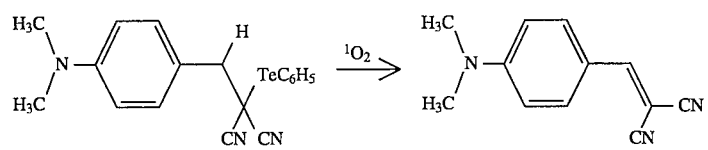

and

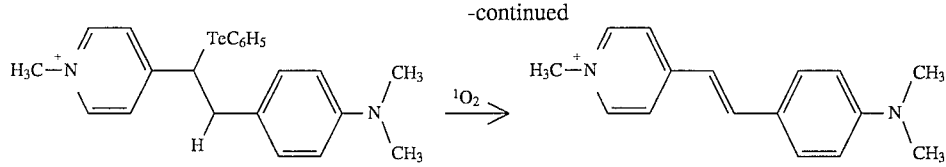

The structure of the photoactive indicator precursor will therefore depend on the particular singlet oxygen reaction that is to be employed and it will usually be designed to assure that any subsequent reactions initiated by reaction with singlet oxygen that are required to produce a photoactive indicator will proceed relatively rapid. Additionally the structure of the photoactive indicator precursor will lead to the formation of a photoactive indicator that has the desired absorption and emission wavelengths, and has relatively high fluorescent quantum yields, preferably >0.1, more preferably greater than 0.4, and a high extinction coefficient at the desired excitation wavelength, preferably >1000 $M^{-1}$ $cm^{-1}$, more preferably >10,000 $M^{-1}$ $cm^{-1}$.

Preferred photoactive indicator precursors of the present invention include compounds containing the following structure (I):

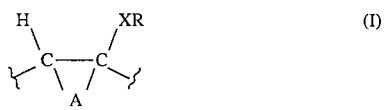

wherein H is cis to the XR group; X is a selenium or tellurium; R is an organic or organometallic group bound to X through an unsaturated carbon atom, a silicon atom, or a tin atom; and A, when taken with the carbon-carbon group, forms an alicyclic ring (optionally fused to one or more aromatic rings) or a heterocyclic ring; where, upon reaction of the compound with singlet oxygen, the H and the XR group are replaced by a carbon-carbon double bond to yield a fluorescent molecule having an extinction coefficient of at least 10,000 $M^{-1}cm^{-1}$ at its absorption maximum and a fluorescence quantum efficiency of at least 10%.

Particularly preferred within these compounds are those compounds wherein X is tellurium. Most preferred is the compound of the following formula:

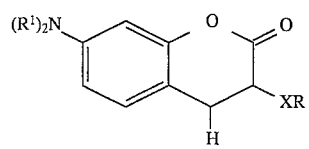

wherein R is an organic or organometallic group bound to X through an unsaturated carbon atom, a silicon atom, or a tin atom; and $R^1$ is hydrogen or alkyl; and wherein up to four of the remaining hydrogen atoms may be replaced by alkyl or alkylene substituents which may be taken together to form one or more alicyclic or aromatic rings.

The compounds disclosed herein containing structure (I) are designated herein as derivatives of the structure, e.g., compound of formula (Ia), compound of formula (If) or compound of formula (Ik). Examples of such compounds where X is tellurium and the fluorescent photoactive indicator molecule formed upon the compounds reaction with singlet oxygen are given below:

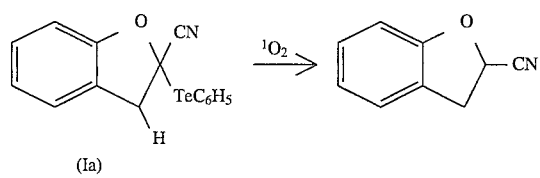

(Ia)

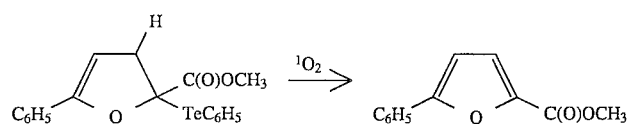

(Ib)

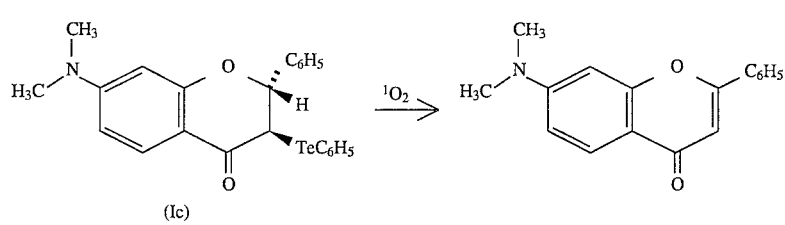

(Ic)

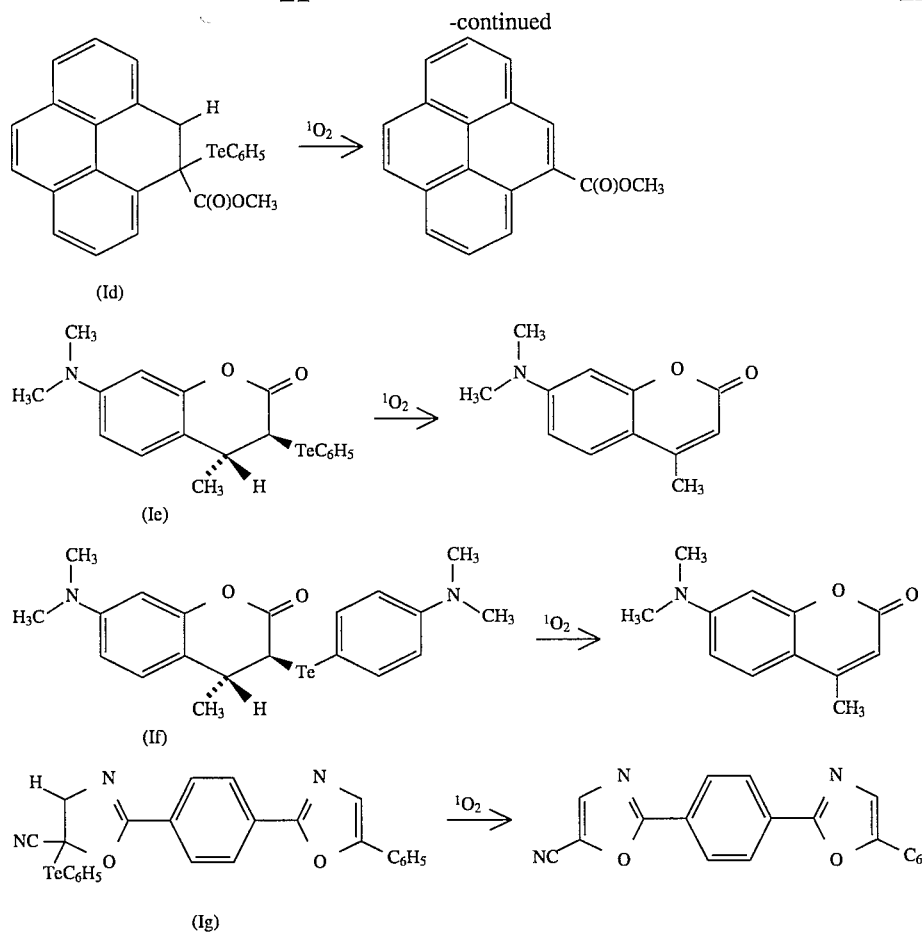

Presently, preferred photosensitive indicator precursors of the invention are the compounds of formula (Ie) and (If) above.

The phenyltelluridyl radical (–TeC$_6$H$_5$) in these compounds can be replaced with other tellurium derivatives, such as TeSiC(CH$_3$)$_3$ and TeSn((CH$_2$)$_3$CH$_3$)$_3$, or the phenyl group can be substituted, preferably with electron donating groups such as –N(CH$_3$)$_2$ and –OCH$_3$. When X is selenium it is preferable that the selenium is substituted by a strong electron donor group or atom, such as tin.

Other classes of photoactive indicator precursors can also be used in the present invention. For example, compounds that chemiluminesce on reaction with singlet oxygen are frequently converted to fluorescent products which can serve as photoactive indicators of the present invention. Examples of such photoactive indicator precursors and the photoactive indicators produced upon reaction with singlet oxygen include the following:

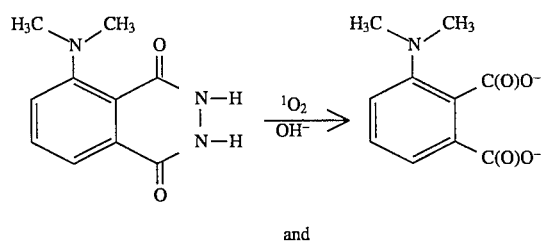

and

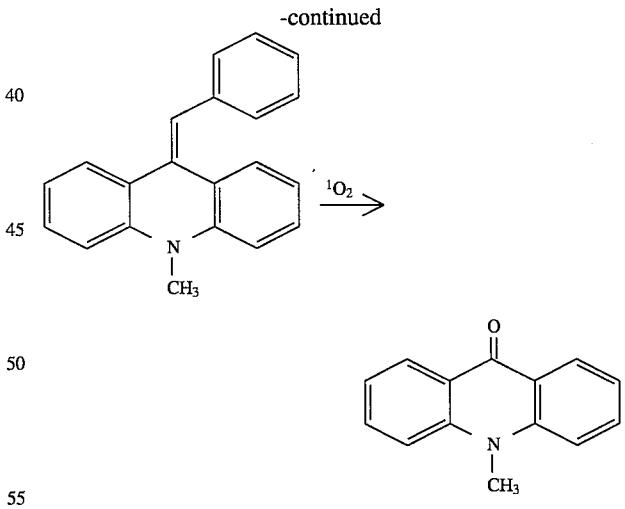

"Photoactive indicator" refers to a molecule which, following absorption of light of wavelengths of 250 to 1100 nm, preferably 300 to 950 nm, emits light by fluorescence or phosphorescence, preferably by fluorescence, or transfers it excitation energy to an acceptor molecule which thereupon emits light by fluorescence or phosphorescence. Preferably the emission quantum yield will be high, usually at least 0.1, preferably at least 0.4, more preferably greater than 0.7 and the extinction coefficient of the absorption maximum will usually be greater than 5000 M$^{-1}$cm$^{-1}$.

Photoactive indicators of this invention are typically fluorescent compounds, such as fluorescent brighteners, which typically absorb light between 300 and 400 nanometers and emit between 400 and 500 nanometers; xanthenes such as rhodamine and fluorescein; bimanes; coumarins such as umbelliferone; aromatic amines such as dansyl; squarate dyes; benzofurans; cyanines, merocyanines, rare earth chelates, and the like. Photoactive indicators that are phosphorescent include porphyrins, phthalocyanines, polyaromatic compounds such as pyrene, anthracene and acenaphthene. Photoactive indicators also include chromenes. Photoactive indicators that can transfer energy to an acceptor molecule will usually absorb at 250 to 550 nm. Such acceptor molecules are luminescent and can include any of the above mentioned fluorescent and phosphorescent photoactive indicators.

"Measuring the fluorescence" refers to the detection and calculation of the amount of light emitted from a photoactive indicator of the invention upon excitation by irradiation with light. While the fluorescence of the photoactive indicator will usually be measured by exciting the photoactive indicator by irradiation with light and simultaneously detecting the light that is emitted therefrom (i.e., the fluorescence), other methods of detecting the fluorescence are contemplated by this invention. The measurement of fluorescence is intended to include detection of light emitted by the photoactive indicator simultaneous with or immediately following irradiation with light regardless of whether the light is absorbed directly or indirectly or whether the emission is from an excited singlet state or state of higher multiplicity. Measurement of fluorescence is also intended to include the measurement of light emitted from the photoactive indicator following transfer of energy from a donor that is excited through chemiexcitation other than chemiexcitation initiated by absorption of light by the photosensitizer. For example, measurement of fluorescence of the photoactive indicator includes activation of a chemiluminescent molecule, for example, by addition of hydrogen peroxide and peroxidase to luminol, and measurement of the light emitted from the photoactive indicator as a result of the energy transfer from the luminol reaction product to the photoactive indicator.

"Support" or "surface" refers to a surface comprised of porous or non-porous water insoluble material. The surface can have any one of a number of shapes, such as strip, rod, particle, including bead, and the like. The surface can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials; glass available as Bioglass, ceramics, metals, and the like. Natural or synthetic assemblies such as liposomes, lipid vesicles, and cells can also be employed.

Binding of sbp members to the support or surface may be accomplished by well-known techniques, commonly available in the literature. See, for example, "Immobilized Enzymes," Ichiro Chibata, Halsted Press, New York (1978) and Cuatrecasas, *J. Biol. Chem.*, 245:3059 (1970).

The surface will usually be polyfunctional or be capable of being polyfunctionalized or be capable of binding a polynucleotide, an sbp member, a photosensitizer, and/or a photoactive chemiluminescent compound through specific or non-specific covalent or non-covalent interactions. A wide variety of functional groups are available or can be incorporated. Functional groups include carboxylic acids, aldehydes, amino groups, cyano groups, ethylene groups, hydroxyl groups, mercapto groups and the like. The manner of linking a wide variety of compounds to surfaces is well know and is amply illustrated in the literature. See for example Cautrecasas, *J. Biol. Chem.* 245,3059 (1970). The length of a linking group to the oligonucleotide or sbp member may vary widely, depending upon the nature of the compound being linked, the effect of the distance between the compound being linked and the surface on the specific binding properties and the like.

"Suspendible particles" refers to particles capable of being able to be suspended in water which are at least about 20 nm and not more than about 20 microns, usually at least about 40 nm and less than about 10 microns, preferably from about 0.10 to 2.0 microns in diameter, and which normally have a volume of less than about 4 picoliters. The suspendible particles may be organic or inorganic, swellable or non-swellable, porous or non-porous, preferably of a density approximating water (generally from about 0.7 to about 1.5 g/ml), and composed of material that can be transparent, partially transparent, or opaque. The suspendible particles will usually be charged, preferably negatively charged. The suspendible particles may be solid (e.g., polymer, metal, glass, organic and inorganic such as minerals, salts and diatoms), oil droplets (e.g., hydrocarbon, fluorocarbon, silicon fluid), or vesicles (e.g., synthetic such as phospholipid or other lipids such as dialkyl phosphates or natural such as cells and organelles). The suspendible particles may be latex particles or other particles comprised of organic or inorganic polymers; lipid vesicles, e.g., liposomes; phospholipid vesicles; oil droplets; silicon particles; metal sols; cells; and dye crystallites.

If organic, the suspendible particles may be polymers, either addition or condensation polymers, which are readily suspendible in the assay medium. The organic suspendible particles will also be adsorptive or functionalizable so as to bind at their surface an sbp member (either directly or indirectly) and to bind at their surface or incorporate within their volume a photosensitizer or a photoactive indicator precursor.

The suspendible particles can be derived from naturally occurring materials, naturally occurring materials which are synthetically modified and synthetic materials. Natural or synthetic assemblies such as lipid bilayers, e.g., liposomes and non-phospholipid vesicles, are preferred. Among organic polymers of particular interest are polysaccharides, particularly cross-linked polysaccharides, such as agarose, which is available as Sepharose, dextran, available as Sephadex and Sephacryl, cellulose, starch, and the like; addition polymers, such as polystyrene, polyacrylamide, homopolymers and copolymers of derivatives of acrylate and methacrylate, particularly esters and amides having free hydroxyl functionalities including hydrogels, and the like. Inorganic polymers include silicones, glasses, available as Bioglas, and the like. Sols include gold, selenium, and other metals. Suspendible particles may also be dispersed water insoluble dyes such as porphyrins, phthalocyanines, etc., which may also act as photosensitizers. Suspendible particles may also include diatoms, cells, viral particles, oil droplets, fat particles such as alkyl triglycerides, magnetosomes, cell nuclei and the like.

Where non-polymeric particles are used, the particle size may be varied by breaking larger particles into smaller particles by mechanical means, such as grinding, sonication, agitation, etc.

Like the surface or support defined above, the suspendible particles will usually be polyfunctional or be capable of being polyfunctionalized or be capable of being bound to an sbp member, photosensitizer, or photoactive indicator precursor through specific or non-specific covalent or non-covalent interactions. A wide variety of functional groups are available or can be incorporated. Exemplary functional groups include carboxylic acids, aldehydes, amino groups, cyano groups, ethylene groups, hydroxyl groups, mercapto groups and the like. When covalent attachment of a sbp member, chemiluminescent compound or photosensitizer to the particle is employed, the manner of linking is well known and is amply illustrated in the literature. See for example Cautrecasas, *J. Biol. Chem.*, 245:3059 (1970). The length of a linking group may vary widely, depending upon the nature of the compound being linked, the nature of the particle, the effect of the distance between the compound being linked and the particle on the binding of sbp members and the analyte and the like.

The photosensitizer and/or photoactive indicator precursor can be chosen to dissolve in, or covalently or bind to suspendible particles, provided, however, that the photosensitizer and the photoactive indicator precursor are not associated with the same particle. When noncovalently bound, the compounds and the particles will all usually be hydrophobic to reduce the ability of the compounds to dissociate from the particles and to associate with the same particle. The problem of having both the photosensitizer and the photoactive indicator associated with the same particle may be minimized by covalently binding either one or both of the compounds to a particle, thereby allowing each compound to be either hydrophilic or hydrophobic.

The number of photosensitizer or photoactive indicator precursor molecules associated with each particle will be at least one and may be sufficiently high enough so that the particle consists entirely of photosensitizer or photoactive indicator precursor molecules. The preferred number of molecules will be selected empirically to provide the highest signal to background in the assay (where the signal is determined under conditions where the particles are bound to each other and the background is determined where the particles are unassociated). Normally, the concentration of photosensitizer and photoactive indicator precursor in the particles will range from $10^{-8}$ to 5M, usually from $10^{-5}$ to $10^{-1}$M, preferably from $10^{-3}$ to $10^{-1}$M.

"Oil droplets" refers to fluid or waxy particles comprised of a lipophilic compound coated and stabilized with an emulsifier that is an amphiphilic molecule such as, for example, phospholipids, sphingomyelin, albumin and the like.

The phospholipids are based upon aliphatic carboxylic acid esters of aliphatic polyols, where at least one hydroxylic group is substituted with a carboxylic acid ester of from about 8 to 36, more usually of from about 10 to 20 carbon atom, which may have from 0 to 3, more usually from 0 to 1 site of ethylenic unsaturation and at least 1, normally only 1, hydroxyl group substituted with phosphate to form a phosphate ester. The phosphate group may be further substituted with small aliphatic compounds which are of di or higher functionality, generally having hydroxyl or amino groups.

The oil droplets can be made in accordance with conventional procedures by combining the appropriate lipophilic compounds with a surfactant, anionic, cationic or nonionic, where the surfactant is present in from about 0.1 to 40, more usually from about 0.1 to 20 weight percent of the mixture and subjecting the mixture in an aqueous medium to agitation, such as sonication or vortexing. Illustrative lipophilic compounds include hydrocarbon oils, halocarbons including fluorocarbons, alkyl phthalates, trialkyl phosphates, triglycerides, etc.

An sbp member will usually be adsorbed to the surface of the oil droplet or bonded directly or indirectly to a surface component of the oil droplet. The sbp member may be incorporated into the liquid particles either during or after the preparation of the liquid particles. The sbp member will normally be present in from about 0.5 to 100, more usually 1 to 90, frequently from about 5 to 80 and preferably from about 50 to 100 mole percent of the molecules present on the surface of the particle.

The following is a list, by way of illustration and not limitation, of amphiphilic compounds, which may be utilized for stabilizing oil droplets: phosphatidyl ethanolamine, phosphatidyl choline, phosphatidyl serine, dimyristoylphosphatidyl choline, egg phosphatidyl choline, diapalmitoylphosphatidyl choline, phosphatidic acid, cardiolipin, lecithin, galactocerebroside, sphingomyelin, dicetylphosphate, phosphatidyl inositol, 2-trihexadecylammoniumethylamine, 1,3-bis(octadecyl phosphate)-propanol, stearoyloxyethylene phosphate, phospholipids, dialkylphosphates, sodium dodecyl sulfate, cationic detergents, anionic detergents, proteins such as albumin, non-ionic detergents, etc.

Stabilization of oil droplets can also be achieved by coating with a polymer such as polycyanoacrylates, dextran, polymerized proteins such as albumin, hydroxybutyl methacrylate, polyacrylamide and the like.

Other compounds may also be used which have lipophilic groups and which have been described previously. For the most part, these compounds will be alkylbenzenes, having alkyl groups of from 6 to 20 carbon atoms, usually mixtures of alkyl groups, which may be straight or branched chain, and having a carboxyl group, an hydroxylic group, a polyoxy alkylene group (alkylene of from 2 to 3 carbon atoms), carboxylic group, sulfonic acid group, or amino group. Aliphatic fatty acids may be used which will normally be of from about 10 to 36, more usually of from about 12 to 20 carbon atoms. Also, fatty alcohols having the carbon limits indicated for the fatty acids, fatty amines of similar carbon limitations and various steroids may also find use.

The oil droplets can comprise a fluorocarbon oil or a silicone oil (silicon particle). Such droplets are described by Giaever in U.S. Pat. Nos. 4,634,681 and 4,619,904 (the disclosures of which are incorporated herein in their entirety). These droplets are formed by dispersing a fluorocarbon oil or silicone oil in an aqueous phase. The droplets are prepared by placing a small amount of the selected oil (generally, such oils are commercially available) in a container with a larger amount of the aqueous phase. The liquid system is subjected to agitation to bring about emulsification and then centrifuged. The homogeneous phase is removed and the residual droplets are resuspended in an aqueous buffered medium. The above centrifugation and decantation steps can be repeated one or more times before the droplets are utilized.

Sbp members can be bound to the droplets in a number of ways. As described by Giaever, the particular sbp member, particularly a proteinaceous sbp member, can be coated on the droplets by introducing an excess of the sbp member into the aqueous medium prior to or after the emulsification step. Washing steps are desirable to remove excess sbp member. Functionalization of the oil introduces functionalities described above for linking to sbp members. Such functionalities can also be employed to link the droplets to a photosensitizer or a photoactive indicator precursor. On the other hand, the photosensitizer or photoactive indicator precursor will frequently be chosen to be soluble in the oil phase of the oil droplet and will not be covalently bound. When the oil is a fluorocarbon, a fluorinated photosensitizer or photoactive indicator precursor will often be more soluble than the corresponding unfluorinated derivation.

"Liposomes" refers to microvesicles of approximately spherical shape and are one of the preferred materials for use in the present invention. The liposomes have a diameter that is at least about 20 nm and not more than about 20 microns, usually at least about 40 nm and less than about 10 microns. Preferably, the diameter of the liposomes will be less than about two microns so as to limit settling or floatation.

The outer shell of a liposome consists of an amphiphilic bilayer that encloses a volume of water or an aqueous solution niposomes with more than one bilayer are referred to as multilamellar vesicles. Liposomes with only one bilayer are called unilamellar vesicles. Multilamellar vesicles are preferred in the present invention when using a lipophilic photosensitizer or photoactive indicator precursor because of their ability to incorporate larger quantities of these materials than unilamellar vesicles. The amphiphilic bilayer is frequently comprised of phospholipids. Phospholipids employed in preparing particles utilizable in the present invention can be any phospholipid or phospholipid mixture found in natural membranes including lecithin, or synthetic glyceryl phosphate diesters of saturated or unsaturated 12-carbon or 24-carbon linear fatty acids wherein the phosphate can be present as a monoester, or as an ester of a polar alcohol such as ethanolamine, choline, inositol, serine, glycerol and the like. Particularly preferred phospholipids include L-α-palmitoyl oleoyl-phosphatidylcholine (POPC), palmitoyl oleoylphosphatidyl-glycerol (POPG), L-α-dioleoylphosphatidylglycerol, L-α-(dioleoyl)-phosphatidyl ethanolamine (DOPE) and L-α-(dioleoyl)-phosphatidyl β-(4-(N-maleimidomethyl)-cyclohexane-1-carboxyamido-)ethanol (DOPE-MCC).

The phospholipids in the bilayer may be supplemented with cholesterol and may be replaced with other amphiphilic compounds that have a polar head group, usually charged, and hydrophobic portion usually comprised of two linear hydrocarbon chains. Examples of such substituents include dialkylphosphate, dialkoxypropylphosphates wherein the alkyl groups have linear chains of 12–20 carbon atoms, N-(2,3-di(9-(Z)-octa-decenyloxy))-prop-1-yl-N,N,N-trimethyl-ammonium chloride (DOTMA), sphingomyelin, cardiolipin, and the like.

Liposomes utilized in the present invention preferably have a high negative charge density to stabilize the suspension and to prevent spontaneous aggregation.

Liposomes may be produced by a variety of methods including hydration and mechanical dispersion of dried phospholipid or phospholipid substitute in an aqueous solution. Liposomes prepared in this manner have a variety of dimensions, compositions and behaviors. One method of reducing the heterogeneity and inconsistency of behavior of mechanically dispersed liposomes is by sonication. Such a method decreases the average liposome size. Alternatively, extrusion is usable as a final step during the production of the liposomes. U.S. Pat. No. 4,529,561 discloses a method of extruding liposomes under pressure through a uniform pore-size membrane to improve size uniformity.

For use in the present invention the liposomes should be capable of binding to an sbp member and be capable of having a photosensitizer or photoactive indicator precursor associated with either the aqueous or the nonaqueous phase. The liposomes utilized in the present invention will usually have sbp members bound to the outer surface of the lipid vesicle.

Preparation of liposomes containing a hydrophobic or amphiphilic photosensitizer or a photoactive indicator precursor dissolved in the lipid bilayer can be carried out in a variety of methods, including a method described by Olsen, et al., *Biochemica et Biophysica Acta*, 557(9), 1979. Briefly, a mixture of lipids containing the appropriate compound in an organic solvent such as chloroform is dried to a thin film on the walls of a glass vessel. The lipid film is hydrated in an appropriate buffer by shaking or vortexing. Thereafter, the lipid suspension is extruded through a series of polycarbonate filter membranes having successively smaller pore sizes, for example, 2.0, 1.0, 0.8, 0.6, 0.4, and 0.2 microns. Repeated filtration through any of the filters, and in particular through the smallest filter, is desirable. The liposomes can be purified by, for example, gel filtration, such as through a column of Sephacryl S-1000. The column can be eluted with buffer and the liposomes collected. Storage in the cold prolongs shelf-life of the liposomes produced by this method. Alternatively the photosensitizer or photoactive indicator precursor can be added to the liquid suspension following preparation of the liposomes.

Labeling of droplets and liposomes will often involve, for example, inclusion of thiol or maleimide or bionin groups on the molecules comprising the lipid bilayer. Photosensitizers, photoactive indicator precursor molecules or sbp members may then be bound to the surface by reaction of the particles with one of these materials that is bound to a sulfhydryl reactive reagent, a sulfhydryl group, or avidin, respectively. Sulfhydryl reactive groups include alkylating reagents such as bromoacetamide and maleimide.

Sbp members can be attracted to the surface of the liposome particles by weak hydrophobic interactions, however such interactions are not generally sufficient to withstand the shear force encountered during incubation and washing. It is preferable to covalently bond sbp members to a liposome particle that has been functionalized, for example by use of DOPE-MCC, as shown above, by combining said liposome with the selected sbp member functionalized with a mercaptan group. For example, if the sbp member is an antibody, it may be reacted with S-acetyl-mercaptosuccinic anhydride (SAMSA) and hydrolyzed to provide a sulfhydryl modified antibody.

"Latex particles" refers to a particulate water-suspendible water-insoluble polymeric material usually having particle dimensions of 20 nm to 20 mm, more preferably 100 to 1000 run in diameter. The latex is frequently a substituted polyethylene such as the following: polystyrene-butadiene, polyacrylamide polystyrene, polystyrene with amino groups, poly-acrylic acid, polymethacrylic acid, acrylonitrile-butadiene, styrene copolymers, polyvinyl acetate-acrylate, polyvinyl pyridine, vinyl-chloride acrylate copolymers, and the like. Non-crosslinked polymers of styrene and carboxylated styrene or styrene functionalized with other active groups such as amino, hydroxyl, halo and the like are preferred. Frequently, copolymers of substituted styrenes with dienes such as butadiene will be used.

The association of the photosensitizer or photoactive indicator precursor with latex particles utilized in the present invention may involve incorporation during formation of the particles by polymerization but will usually involve incorporation into preformed particles, usually by noncovalent dissolution into the particles. Usually a solution of the photoactive indicator precursor or photosensitizer will be employed. Solvents that may be utilized include alcohols (including ethanol), ethylene glycol and benzyl alcohol;

amides such as dimethyl formamide, formamide, acetamide and tetramethyl urea and the like; sulfoxides such as dimethyl sulfoxide and sulfolane; and ethers such as carbitol, ethyl carbitol, dimethoxy ethane and the like, and water. The use of solvents having high boiling points in which the particles are insoluble permits the use of elevated temperatures to facilitate dissolution of the compounds into the particles and are particularly suitable. The solvents may be used singly or in combination. Particularly preferred solvents for incorporating a photosensitizer are those that will not quench the triplet excited state of the photosensitizer either because of their intrinsic properties or because they can subsequently be removed from the particles by virtue of their ability to be dissolved in a solvent such as water that is insoluble in the particles. Aromatic solvents are preferred, and generally solvents that are soluble in the particle. For incorporating photoactive indicator precursors in particles a solvent should be selected that does not interfere with the fluorescence of the photoactive indicator so formed because of their intrinsic properties or ability to be removed from the particles. Frequently, aromatic solvents will also be preferred. Typical aromatic solvents include dibutylphthalate, benzonitrile, naphthonitrile, dioctylterephthalate, dichlorobenzene, diphenylether, dimethoxybenzene, etc.

Except when the photosensitizer or photoactive indicator precursor is to be covalently bound to the particles, it will usually be preferable to use electronically neutral photosensitizers or photoactive indicator precursors. It is preferable that the liquid medium selected does not soften the polymer beads to the point of stickiness. A preferred technique comprises suspending the selected latex particles in a liquid medium in which the photosensitizer or photoactive indicator precursor has at least limited solubility. Preferably, the concentrations of the photosensitizer and photoactive indicator precursor in the liquid media will be selected to provide particles that have the highest efficiency of singlet oxygen formation and highest quantum yield of emission from the photoactive indicator so formed in the media but less concentrated solutions will sometimes be preferred. Distortion or dissolution of the particles in the solvent can be prevented by adding a miscible cosolvent in which the particles are insoluble.

Generally, the temperature employed during the procedure will be chosen to maximize the singlet oxygen formation ability of the photosensitizer-labeled particles and the quantum yield of the photoactive indicator so formed from the photoactive indicator precursor-labelled particles with the proviso that the particles should not become aggregated at the selected temperature. Elevated temperatures are normally employed. The temperatures for the procedure will generally range from 20° C. to 200° C., more usually from 50° C. to 170° C. It has been observed that some compounds that are nearly insoluble in water at room temperature, are soluble in, for example, low molecular weight alcohols, such as ethanol and ethylene glycol and the like, at elevated temperatures. Carboxylated modified latex particles have been shown to tolerate low molecular weight alcohols at such temperatures.

An sbp member may be physically adsorbed on the surface of the latex particle or may be covalently bonded to the particle. In cases wherein the sbp member is only weakly bound to the surface of the latex particle, the binding may in certain cases be unable to endure particle-to-particle shear forces encountered during incubation and washings. Therefore, it is usually preferable to covalently bond sbp members to the latex particles under conditions that will minimize adsorption. This may be accomplished by chemically activating the surface of the latex. For example, the N-hydroxysuccinimide ester of surface carboxyl groups can be formed and the activated particles to reduce nonspecific binding of assay components to the particle surface are then contacted with a linker having amino groups that will react with the ester groups or directly with an sbp member that has an amino group. The linker will usually be selected to reduce nonspecific binding of assay components to the particle surface and will preferably provide suitable functionality for both attachment to the latex particle and attachment of the sbp member. Suitable materials include maleimidated aminodextran (MAD), polylysine, aminosaccharides, and the like. MAD can be prepared as described by Hubert, et al., *Proc. Natl. Acad. Sci.*, 75(7), 3143, 1978.

In one method, MAD is first attached to carboxyl-containing latex particles using a water soluble carbodiimide, for example, 1-(3-dimethylaminopropyl)-3-ethyl carbodiimide. The coated particles are then equilibrated in reagents to prevent nonspecific binding. Such reagents include proteins such as bovine gamma globulin (BGG), and detergent, such as Tween 20, TRITON X-100 and the like. A sbp member having a sulfhydryl group, or suitably modified to introduce a sulfhydryl group, is then added to a suspension of the particles, whereupon a covalent bond is formed between the sbp member and the MAD on the particles. Any excess unreacted sbp member can then be removed by washing.

"Metal sols" refers to those suspendible particles comprised of a heavy metal, i.e., a metal of atomic number greater than 20 such as a Group IB metal, e.g., gold or silver.

Metal sol particles are described, for example, by Leuvering in U.S. Pat. No. 4,313,734, the disclosure of which is incorporated herein by reference in its entirety. Such sols include colloidal aqueous dispersion of a metal, metal compound, or polymer nuclei coated with a metal or metal compound.

The metal sols may be of metals or metal compounds, such as metal oxides, metal hydroxides and metal salts or of polymer nuclei coated with metals or metal compounds. Examples of such metals are platinum, gold, silver mercury, lead, palladium, and copper, and of such metal compounds are silver iodide, silver bromide, copper hydrous oxide, iron oxide, iron hydroxide or hydrous oxide, aluminum hydroxide or hydrous oxide, chromium hydroxide or hydrous oxide, vanadium oxide, arsenic sulphide, manganese hydroxide, lead sulphide, mercury sulphide, barium sulphate and titanium dioxide. In general, the metals or metal compounds useful may be readily demonstrated by means of known techniques.

It is sometimes advantageous to use sols comprised of dispersed particles consisting of polymer nuclei coated with the above mentioned metals or metal compounds. These particles have similar properties as the dispersed phase of pure metals or metal compounds, but size, density and metal contact can be optimally combined.

The metal sol particles may be prepared in a large number of ways which are in themselves known. For example, for the preparation of a gold sol Leuvering refers to an article by G. Frens in *Nature Physical Science* 241, 20 (1973).

The metal sol particles can be modified to contain various functional groups as described above for linking to an sbp member or a photosensitizer or a photoactive indicator precursor. For example, polymeric bonding agents can be used to coat the particles such as polymers containing thiol groups that bond strongly to many heavy metals or silylating agents that can bond and form polymeric coatings as, for example, by reaction of metal particles with trialkoxy aminoalkylsilanes as described in European Published Patent Application 84400952.2 by Advanced Magnetics for coating magnetic particles.

"Dye crystallites" refers to microcrystals of pure or mixed solid water insoluble dyes, preferably dyes that can serve as the photosensitizers described above. The dye crystallites useful in the present invention have a size range of 20 nm to 20 μm.

One method for preparing dye crystallites is described in U.S. Pat. No. 4,373,932 (Gribnau, et al.), the disclosure of which is incorporated herein by reference in its entirety. Gribnau describes colloidal dye particles and aqueous dispersions of a hydrophobic dye or pigment, which may have an immunochemically reactive component directly or indirectly attached. The dye particles are prepared in general by dispersing a dye in water and then centrifuging. A dye pellet is obtained and resuspended in water, to which glass beads are added. This suspension is rolled for several days at room temperature. The liquid is decanted and centrifuged, and the dye particles are obtained after aspiration of the liquid.

Another method for preparing dye crystallites is by slow addition of a solution of the dye in a water miscible solvent to water. Another method is by sonication of a suspension of the solid dye in water.

Binding of sbp members to the dye particles can be achieved by direct or indirect adsorption or covalent chemical attachment. The latter is governed by the presence of suitable functional groups in any coating material and in the dye. For example, functional groups can be introduced onto the surface of a dye crystalline by coupling a compound containing a diazotized aromatic amino group and the desired functional group to a phenolic or anilino group of the dye.

Where the dye has a carboxyl group, the dye crystallite can be activated by a carbodiimide and coupled to a primary amino component. Aliphatic primary amino groups and hydroxyl groups can be activated, for example, by cyanogen bromide or halogen-substituted di- or tri-azines, after which attachment with a primary amino component or, for example, with a component containing a —SH or —OH group can take place. Use can also be made of bifunctional reactive compounds. For example, glutaraldehyde can be used for the mutual coupling of primary amino components of the dye and an sbp member, and, for example, a heterobifunctional reagent such as N-succinimidyl 3-(2-pyridyldithio) propionate can be employed for the coupling of a primary amino component to a component containing a thiol group.

"Wholly or partially sequentially" refers to the condition when the components of the methods of the present invention are combined other than concomitantly (simultaneously), one or more may be combined with one or more of the remaining agents to form a subcombination. Each subcombination can then be subjected to one or more steps of the present method. Thus, each of the subcombinations can be incubated under conditions to achieve one or more of the desired results.

Various ancillary materials will frequently be employed in the assay in accordance with the present invention. For example, buffers will normally be present in the assay medium, as well as stabilizers for the assay medium and the assay components. Frequently, in addition to these additives, proteins may be included, such as albumins, organic solvents such as formamide, quaternary ammonium salts, polycations such as dextran sulfate, surfactants, particularly non-ionic surfactants, binding enhancers, e.g., polyalkylene glycols, or the like.

DESCRIPTION OF THE SPECIFIC EMBODIMENTS

In general, the present invention is directed to methods for determining an analyte in a selected medium. The methods comprise treating a medium suspected of containing an analyte under conditions such that the analyte, if present, affects the amount of a photosensitizer and a photoactive indicator precursor that can come into close proximity wherein the short-lived singlet oxygen generated by the photosensitizer can react with the photoactive indicator precursor prior to the spontaneous decay of the singlet oxygen in order to form a photoactive indicator. The method further comprises exposing the photoactive indicator to light which may be of the same or a different wavelength that the light used to excite the photosensitizer in order to excite the photoactive indicator so formed and then measuring the intensity of fluorescence emitted from the photoactive indicator upon excitation. The intensity of fluorescence produced is related to the amount of analyte in the medium. The photoactive indicator is formed upon reaction of the photoactive indicator precursor with the singlet oxygen generated by the photosensitizer. The photosensitizer catalyzes the generation of singlet oxygen usually in response to photoexcitation followed by energy transfer to molecular oxygen. Often one or both of the photosensitizer and the photoactive indicator precursor will be associated with surfaces, wherein, in homogeneous assays, the surface will preferably be the surface of suspendible particles.

For homogeneous assays the invention is predicated on an analyte causing or inhibiting molecules of the photosensitizer and the photoactive indicator precursor to be closer to each other than their average distance in the bulk solution of the assay medium. The amount of this partitioning will depend upon the amount of analyte present in the sample to be analyzed. The photosensitizer molecules that do not become associated with the photoactive indicator precursor produce singlet oxygen that is unable to reach the photoactive indicator precursor before undergoing decay in the aqueous medium. However, when the photosensitizer and the photoactive indicator precursor come in close proximity with each other in response to the presence of the analyte, the singlet oxygen produced upon irradiation of the photosensitizer can react with the photoactive indicator precursor to form a photoactive indicator before undergoing decay. Because numerous photoactive indicator precursor molecules and/or photosensitizer molecules can be associated with a surface or can be incorporated into the material comprising the surface, the presence of a surface in conjunction with the photosensitizer and photoactive indicator precursor can increase the efficiency of, or action of, singlet oxygen with the photoactive indicator precursor prior to decay. It is therefore preferred to bring one member of the photoactive indicator precursor and photosensitizer pair into the proximity of a surface that incorporates the other member as a function of the presence of an analyte. The subject assay provides for a convenient method for detecting and measuring a wide variety of analytes in a simple, efficient, reproducible manner, which can employ simple equipment for measuring the amount of light produced during the reaction.

The amount of photosensitizer that comes in close proximity to the photoactive indicator precursor is affected by the presence of analyte by virtue of the photosensitizer and photoactive indicator precursor each being associated with an sbp member. This may be accomplished in a number of ways and the term "associated with" is defined thereby. The photosensitizer and photoactive indicator precursor may contain functionalities for covalent attachment to sbp members and the sbp members may contain functionalities for attaching to the photosensitizer and/or photoactive indicator precursor. The attachment may be accomplished by a direct bond between the two molecules or through a linking group which can be employed between an sbp member and the photosensitizer or photoactive indicator precursor. In another embodiment either or both of the photosensitizer and photoactive indicator precursor can be bound to surfaces or incorporated in particles, to which are also attached sbp members. In both cases each of the sbp members is capable of binding directly or indirectly to the analyte or an assay component whose concentration is affected by the presence of the analyte. Either or both of the photosensitizer and photoactive indicator precursor can be incorporated into particles by virtue of being dissolved in at least one phase of the particles, in which case the solute will be at much higher concentration within the particle than in the bulk assay medium.

Alternatively, either or both of the photosensitizer and photoactive indicator precursor my be covalently bound to particles, either by providing linking functional groups on the components to be bound or by incorporating the photosensitizer or photoactive indicator precursor into a polymer that comprises the particles. For particles that are oil droplets or liposomes the photosensitizer and photoactive indicator precursor can be attached to one or more long hydrocarbon chains, each generally having at least 10 to 30 carbon atoms. If the particles are droplets of a fluorocarbon, the photosensitizer or photoactive indicator precursor incorporated into these particles may be fluorinated to enhance solubility and reduce exchange into other particles bound with the other label, and the hydrocarbon chain used for linking will preferably be replaced with a fluorocarbon chain. For silicon fluid particles the photosensitizer and photoactive indicator precursor can be bound to a polysiloxane. In order to maximize the number of photosensitizer or photoactive indicator precursor molecules per particle, it will usually be desirable to minimize the charge and polarity of the photosensitizer or photoactive indicator precursor so that it resides within the non-aqueous portion of the particle. When the particle is a liposome and it is desired to retain the photosensitizer or photoactive indicator precursor in the aqueous phase of the liposome, it will be preferred to use photosensitizers or photoactive indicator precursors that are highly polar or charged.

No matter how the photosensitizer and the photoactive indicator precursor are associated with their respective sbp member, it is critical that neither compound is capable of dissociating from its sbp member and becoming associated with the sbp member associated with the other member of the photosensitizer and photoactive indicator precursor pair during the course of the assay. Thus, dissociation of these compounds from their respective sbp members must be slow relative to the time required for the assay.

The photoactive indicator precursor may be bound to a sbp member that is capable of binding directly or indirectly to the analyte or to an assay component whose concentration is affected by the presence of the analyte. The term "capable of binding directly or indirectly" means that the designated entity can bind specifically to the entity (directly) or can bind specifically to a specific binding pair member or to a complex of two or more sbp members which is capable of binding the other entity (indirectly).

The surface generally has an sbp member bound to it. Preferably, the photoactive indicator precursor is associated with the surface, usually within a suspendible particle. This sbp member is generally capable of binding directly or indirectly to the analyte or a receptor for the analyte. When the sbp members associated with the photosensitizer and the photoactive indicator precursor are both capable of binding to the analyte, a sandwich assay protocol can be used. When one of the sbp members associated with the photosensitizer or photoactive indicator precursor can bind both the analyte and an analyte analog, a competitive assay protocol can be used. The attachment to a surface or incorporation in a particle of the photoactive indicator precursor is governed generally by the same principles described above for the attachment to, or the incorporation into, a particle of the photosensitizer.

The photosensitizer is usually caused to activate the photoactive indicator precursor by irradiating the medium containing these reactants. Since it will frequently be undesirable to excite the photoactive indicator precursor directly with light, the wavelength of light used to activate the photosensitizer will usually be longer than the longest wavelengths absorbed substantially by the photoactive indicator precursor. However, the medium must be irradiated with a short enough wavelength of light that has sufficient energy to convert the photosensitizer to an excited state and thereby render it capable of activating molecular oxygen to singlet oxygen. The excited state for the photosensitizer capable of exciting molecular oxygen is generally a triplet state which is more than about 20, usually at least 23 Kcal/mol more energetic than the photosensitizer ground state. Preferably, the medium is irradiated with light having a wavelength of about 450 to 950 nm, although shorter wavelengths can be used, for example, 230–950 nm, and longer wavelengths of up to 2000 nm can be used by providing sufficiently intense light to provide for biphotonic excitation.

Although it will usually be preferable to excite the photosensitizer by irradiation with light of a wavelength that is efficiently absorbed by the photosensitizer, other means of excitation may be used, for example, by energy transfer from an excited state of an energy donor. When an energy donor is used, wavelengths of light can be used which are inefficiently absorbed by the photosensitizer but are efficiently absorbed by the energy donor. The energy donor may be bound to an assay component that is associated, or becomes associated, with the photosensitizer, for example, bound to a surface or incorporated in the particle having the photosensitizer. When an energy donor is employed its lowest energy singlet and/or triplet state will usually be of higher energy than the lowest energy singlet and/or triplet state, respectively, of the photosensitizer.

The singlet oxygen so formed reacts with the photoactive indicator precursor to form a photoactive indicator which is fluorescent. Fluorescence of the photoactive indicator that is formed can be detected following electronic excitation of the photoactive indicator. Normally electromagnetic radiation, preferably light, will be used to excite the photoactive indicator, but energy transfer from molecules that have been excited by other means such as chemiexcitation can also be used when the chemiexcitation is separate from the abovementioned singlet oxygen reaction. The wavelength of light used to excite the photoactive indicator can be the same or different from the wavelength of light used to excite the photosensitizer. Usually it will be preferable for the light emitted by the photoactive indicator to be shorter wavelength than any fluorescence of the photosensitizer. Preferably, therefore, when the photosensitizer is fluorescent, the light used to excite the photoactive indicator will be shorter wavelength than that used to activate the photosensitizer, usually at least 50 nm shorter, preferably at least 200 nm shorter. The fluorescence emitted from the excited photoactive indicator my be measured in any convenient manner such as photographically, visually or photometrically, to determine the amount thereof, which is related to the amount of analyte in the medium.

Irradiation of the photosensitizer and the excitation of the photoactive indicator may be carried out simultaneously but will preferably be carried out sequentially so that the light used to excite the photosensitizer does not interfere with the fluorescence measurement. The photoactive indicator precursor must not substantially absorb light at the wavelength used to generate the singlet oxygen and will therefore usually absorb at shorter wavelengths than the photosensitizer. In addition, the photoactive indicator precursor will preferably not absorb significantly at the wavelength required to excite the photoactive indicator and therefore will usually absorb at shorter wavelengths than the photoactive indicator.

The method and compositions of the invention may be adapted to most assays involving sbp members such as ligand-receptor; e.g., antigen-antibody reactions; polynucleotide binding assays, and so forth. The assays may be homogeneous or heterogeneous, competitive or noncompetitive. The assay components, photoactive indicator precursor and photosensitizer, can be associated in a number of ways to a receptor, to a ligand, or, when employed, to an surface. The association may involve covalent or noncovalent bonds. Those skilled in the art will be able to choose appropriate associations depending on the particular assay desired in view of the foregoing and the following illustrative discussion.

The sample may be pretreated if necessary to remove unwanted materials. The reaction for a noncompetitive sandwich type assay can involve an sbp member, (e.g., an antibody, polynucleotide probe, receptor or ligand) complementary to the analyte and associated with a photoactive indicator precursor; a photosensitizer associated with an sbp member, (e.g., antibody, polynucleotide probe, receptor or ligand) that is also complementary to the analyte; the sample of interest; and any ancillary reagents required. In a competitive protocol one sbp member can be a derivative of the analyte and the other sbp member can be complementary to the analyte, e.g., an antibody. In either protocol the components may be combined either simultaneously or wholly or partially sequentially. The ability of singlet oxygen produced by an activated photosensitizer to react with the photoactive indicator precursor to form a photoactive indicator is governed by the binding of an sbp member to the analyte. Hence, the presence or amount of analyte can be determined by measuring the amount of light emitted upon activation of the photoactive indicator so formed by irradiation. Both the binding reaction and detection of the extent thereof can be carried out in a homogeneous solution without separation, wherein, preferably, one or both of the photosensitizer and the photoactive indicator precursor are incorporated in particles to which the sbp members are attached. This is an advantage of the present invention over prior art methods utilizing chemiluminescence.

In a heterogeneous assay approach, one of the sbp members will frequently be bound to a support or another means provided to separate it from the assay medium. The support may be either a non-dispersible surface or a particle. In one embodiment, the support or particle will have associated with it one member of a group consisting of the photoactive indicator precursor and the photosensitizer. Another sbp member will have the other member of the group associated with it wherein the sbp members can independently, either directly or indirectly, bind the analyte or a receptor for the analyte. These components are generally combined either simultaneously or wholly or partially sequentially. The surface or particles are then separated from the liquid phase and either are subjected to conditions for activating the photosensitizer and the photoactive indicator so formed, usually by irradiating the separated phase, and measuring the amount of fluorescence emitted.

Alternatively, a hererogenous assay of this invention may be carried out by providing means such as a surface to separate a first sbp member from the liquid assay medium and providing a second sbp member that is associated with a photosensitizer and that binds to the first sbp member as a function of the amount of analyte in the medium. The sample suspected of containing the analyte is then combined with the first and second sbp members either simultaneously or wholly or partially sequentially and the first sbp member is separated from the medium. A third sbp member associated with a photoactive indicator precursor is then combined with the separated first sbp member where the third sbp member is capable of binding directly or indirectly to the second sbp member. The combination is then irradiated to activate the photosensitizer and the fluorescence of the photoactive indicator so formed is measured.

The binding reactions in an assay for the analyte will normally be carried out in an aqueous medium at a moderate pH, generally that which provides optimum assay sensitivity. Preferably, the activation of the photosensitizer will also be carried out in an aqueous medium. However, when a separation step is employed, non-aqueous media such as, e.g., acetonitrile, acetone, toluene, benzonitrile, etc. and aqueous media with pH values that are very high, i.e., greater than 10.0, or very low, i.e., less than 4.0, preferably with pH values that are very high, can be used. As explained above, the assay can be performed either without separation (homogeneous) or with separation (heterogeneous) of any of the assay components or products.

The aqueous medium my be solely water or may include from 0.01 to 80 volume percent of a cosolvent but will usually include less than 40% of a cosolvent when an sbp member is used that is a protein. The pH for the medium of the binding reaction will usually be in the range of about 4 to 11, more usually in the range of about 5 to 10, and preferably in the range of about 6.5 to 9.5. The pH will usually be a compromise between optimum binding of the binding members and the pH optimum for the production of signal and the stability of other reagents of the assay. Usually no change in pH will be required for signal production, although if desired, a step involving the addition of an acid or a basic reagent can be inserted between the binding reaction and generation of singlet oxygen and/or signal production. Usually in homogenous assays the final pH will be in the range of 5–13. For hererogenous assays non-aqueous solvents may also be used as mentioned above, the main consideration being that the solvent not react efficiently with singlet oxygen.

Various buffers may be used to achieve the desired pH and maintain the pH during an assay. Illustrative buffers include borate, phosphate, carbonate, tris, barbital and the like. The particular buffer employed is not critical to this invention, but in an individual assay one or another buffer may be preferred.

Moderate temperatures are normally employed for carrying out the binding reactions of proteinaceous ligands and receptors in the assay and usually constant temperature, preferably, 25° to 40°, during the period of the measurement. Incubation temperatures for the binding reaction will normally range from about 5° to 45° C., usually from about 15° to 40° C., more usually 25° to 40° C. Where binding of nucleic acids occur in the assay, higher temperatures will frequently be used, usually 20° to 90°, more usually 35° to 75° C. Temperatures during measurements, that is, generation of singlet oxygen and light detection, will generally range from about 20° to 100°, more usually from about 25° to 50° C., more usually 25° to 40° C.

The concentration of analyte which may be assayed will generally vary from about $10^{-4}$ to below $10^{-16}$M, more usually from about $10^{-6}$ to $10^{-14}$M. Considerations, such as whether the assay is qualitative, semiquantitative or quantitative, the particular detection technique the concentration of the analyte of interest, and the maximum desired incubation times will normally determine the concentrations of the various reagents.

In competitive assays, while the concentrations of the various reagents in the assay medium will generally be determined by the concentration range of interest of the analyte, the final concentration of each of the reagents will normally be determined empirically to optimize the sensitivity of the assay over the range. That is, a variation in concentration of the analyte which is of significance should provide an accurately measurable signal difference.

The concentration of the sbp members will depend on the analyte concentration, the desired rate of binding, and the degree that the sbp members bind nonspecifically. Usually, the sbp members will be present in at least the lowest expected analyte concentration, preferably at least the highest analyte concentration expected, and for noncompetitive assays the concentrations may be 10 to $10^{-6}$ times the highest analyte concentration but usually less than $10^{-4}$M, preferably less than $10^{-6}$M, frequently between $10^{-11}$ and $10^{-7}$M. The amount of photosensitizer or photoactive indicator precursor associated with a sbp member will usually be at least one molecule per sbp member and may be as high as $10^5$, usually at least $10$–$10^4$ when the photosensitizer or photoactive indicator precursor molecule is incorporated in a particle.

While the order of addition may be varied widely, there will be certain preferences depending on the nature of the assay. The simplest order of addition is to add all the materials simultaneously. Alternatively, the reagents can be combined wholly or partially sequentially. When the assay is competitive, it will often be desirable to add the analyte analog after combining the sample and an sbp member capable of binding the analyte. Optionally, an incubation step may be involved after the reagents are combined, generally ranging from about 30 seconds to 6 hours, more usually from about 2 minutes to 1 hour before the photosensitizer is caused to generate singlet oxygen and the photoactive indicator is caused to fluoresce.

In a particularly preferred order of addition, a first set of sbp members that are complementary to and/or homologous with the analyte are combined with the analyte followed by the addition of specific binding pair members complementary to the first specific binding pair members, each associated with a different member of the group consisting of a photosensitizer and a photoactive indicator precursor. The assay mixture, or a separated component thereof, is irradiated first to produce singlet oxygen and then later to produce measurable fluorescence.

In a homogeneous assay after all of the reagents have been combined, they can be incubated, if desired. Then, the combination is irradiated (at the necessary wavelengths of light) and the resulting fluorescence emitted is measured. The emitted fluorescence is related to the amount of the analyte in the sample tested. The amounts of the reagents of the invention employed in a homogeneous assay depend on the nature of the analyte. Generally, the homogeneous assay of the present invention exhibits an increased sensitivity over known assays such as the EMIT® assay. This advantage results primarily because of the improved signal to noise ratio obtained in the present method.

The following assays are provided by way of illustration and not limitation to enable one skilled in the art to appreciate the scope of the present invention and to practice the invention without undue experimentation. It will be appreciated that the choice of analytes, photosensitizers, photoactive indicator precursors, surfaces, particles and reaction conditions will be suggested to those skilled in the art in view of the disclosure herein in the examples that follow.

In one embodiment of the invention a photoactive indicator precursor of the following formula (Im):

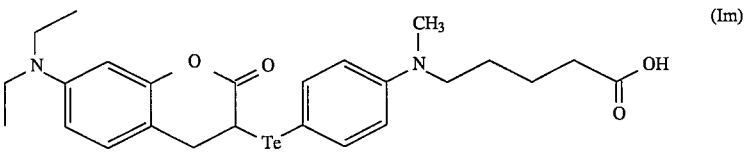

is covalently linked to an antibody for human chorionic gonadotropin (HCG) to provide Reagent 1. The photoactive indicator precursor, functionalized with a N-hydroxysuccinimidyl ester of the carboxyl group, reacts with the amino groups of the antibody. The linking group is a carboxamide. The photosensitizer utilized is rose bengal, which is covalently bound to latex particles having an average dimension of 0.5 micron. The latex particles and rose bengal are covalently bound to each other by means of chloromethyl groups on the latex to provide an ester linking group as described in *J. Am. Chem. Soc.*, 97:3741 (1975). The latex particle is further linked to a second antibody for HCG by means of N-hydroxysuccinimidyl ester groups on the latex to provide Reagent 2. Both of the antibodies employed are monoclonal antibodies prepared by standard hybrid cell line technology. One antibody recognizes the α-subunit of HCG and the other recognizes the β-subunit of HCG. In conducting the assay a serum sample suspected of containing HCG is obtained from a patient. Fifty microliters of the sample is combined in a 500 microliters of aqueous medium, buffered with Tris buffer at pH 8.0, with Reagent 1 and Reagent 2 above. The amounts of Reagent 1 and Reagent 2 are sufficient to provide concentrations of each antibody of about $10^{-9}$ molar. The reaction mixture is then incubated for a period of one hour at 25° C. and then irradiated for 30 minutes with 560 nm light. The fluorescence of the solution is then measured by irradiating at 350 nm and detecting at 440 nm and is compared with values obtained in a similar procedure with samples having known concentrations of HCG to determine the concentration of HCG in the unknown.

In an alternative approach based on the above, Reagent 2 is rose bengal covalently linked to the second antibody and no latex particle is employed. In still another alternative approach based on the above, Reagent 2 is rose bengal covalently linked to the second antibody and Reagent 1 is the photoactive indicator precursor covalently bound to latex particles, to which the first antibody is covalently attached. In still another alternative approach based on the above, Reagent 1 is as described immediately above, Reagent 2 is rose bengal covalently linked to latex particles, to which avidin is covalently attached, and a third reagent (Reagent 2A) that is the second antibody covalently linked to biotin is employed. Reagent 1 and the third reagent are combined with sample and incubated. Then, an excess of Reagent 2 is added and the reining procedure is as described above.

In another embodiment in accordance with the present invention, a first set of oil droplets (Reagent 3) is prepared from a solution of the photosensitizer and chlorophyll in mineral oil in accordance with Giaever, supra. The oil droplets, which range from 0.1 to 2 microns in diameter, are coated with a functionalized surfactant that is linked to a monoclonal antibody for C-reactive protein (CRP). The chlorophyll is lipophilic and is therefore dissolved in the lipophilic oil droplet. A second set of oil droplets (Reagent 4) is prepared in a similar manner. In this set of droplets the oil droplet is similarly coated with a second monoclonal antibody for CRP, which recognizes a different portion of the CRP molecule than that recognized by the first monoclonal antibody referred to above. 9-Benzal-10-methyl acridan is irreversibly dissolved in the lipophilic oil droplet by including a N,N-didodecylcarboxamide group bound to one of the phenyl groups of the acridan. The monoclonal antibodies are prepared by standard hybrid cell line technology. A serum sample suspected of containing CRP (50 microliters) is combined with excess quantities of Reagent 3 and Reagent 4 in an aqueous buffered medium (500 µL) at pH 7.5. The medium is incubated at 25° C. for a period of 20 minutes. The medium, without separation, is irradiated at 633 nm using a HeNs laser for a period of twenty minutes and the fluorescence of the solution is measured by irradiation at 360 nm and detection at 440 nm of the light emitted. The intensity of fluorescence is compared with that from samples containing known amounts of CRP and the amount of CRP in the unknown sample is determined by comparing the values. In this way a convenient and sensitive homogeneous immunoassay for CRP is conducted.

In an alternative approach based on the above, Reagent 3 has an antibody for fluorescein in place of the antibody for CRP and an additional reagent (Reagent 3A) has the CRP antibody covalently linked to fluorescein. Reagent 4 has avidin in place of the second CRP antibody and a fourth reagent (Reagent 4A) has the second antibody covalently linked to biotin. In the assay Reagent 4A and Reagent 3A are combined with sample and incubated. Thereafter, Reagents 3 and 4 are added and incubated. The remainder of the assay procedure as described above is then carried out.

In another embodiment of the present invention, one set of liposomes (Reagent 5) (0.2 micron in diameter) is formed by high pressure extrusion of a phospholipid suspension in pH 7.4 buffer through a 0.2 micron pore membrane using a commercially available instrument designed for such purpose. A thyroxine analog is covalently linked to the liposome by first forming mercaptoacetamide groups on the liposome by reaction of phosphatidylethanolamine in the liposome with an N-hydroxysuccinimide ester of methyl carboxym-ethyl disulfide followed by reaction with dithioerythritol. Bromoacetyl thyroxine is then allowed to react with the sulfhydrylated liposomes. A metallo-porphyrin dye is dissolved in the lipophilic portion of the liposome. Another set of liposomes (Reagent 6) is utilized to attach a monoclonal antibody for thyroxine. The antibody is attached covalently by means similar to the attachment of thyroxine. A photoactive indicator precursor of the following formula:

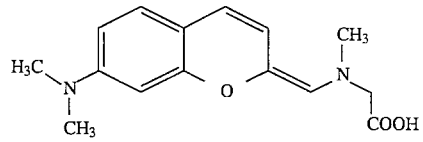

is covalently linked by means of a carboxamide linking group to the surface of the liposome. Reagent 5 and Reagent 6 are combined in an aqueous buffered assay medium (500 µL) of pH 8.0 together with a serum sample suspected of containing thyroxine that contains a thyroxine releasing agent of the following formula:

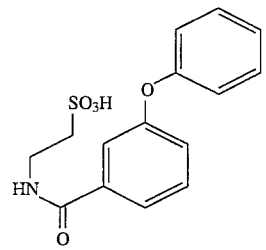

to displace thyroxine from binding proteins (50 microliters). The assay medium is then incubated at room temperature for 1 hour. The medium is irradiated at 650 nm for a period of 1 minute and the fluorescence is measured as in the preceding examples. The value obtained is compared with values obtained by conducting a similar assay with known amounts of thyroxine. In this way the amount of thyroxine in the serum sample is quantitated.

In an alternative approach based on the above, Reagent 6 has avidin in place of antibody for thyroxine. An additional reagent (Reagent 6A) has antibody for thyroxine covalently linked to biotin. Reagent 5 has antibody for fluorescein in place of thyroxine and an additional reagent (Reagent 5A) has thyroxine linked covalently to fluorescein. In the assay Reagents 5A and 6A are combined with sample and incubated. Then, Reagent 5 and 6 are added, the mixture is incubated, and the remainder of the assay procedure is followed.

In another embodiment 2-hydroxyethyl-9,10-dibromoanthracene is formed into a dye crystallite in a manner similar to that described by Gribnau. A 25mer oligonucleotide probe that recognizes a sequence of hepatitis B RNA is covalently attached to the dye crystallite by means of a carbamate linking group. A second 25mer oligonucleotide probe for hepatitis B RNA is covalently linked to 9-(benzal-9H-xanthene) by means of an amide linking group. The dye crystallite has a particle size 2 microns on the average. The oligonucleotides are prepared by standard automated synthesis technology. A sample (50 µL) from a patient suspected of having hepatitis B is combined in an aqueous assay medium (500 µL) at pH 7.0 with an excess of the dye crystallite and the second probe described above. The assay medium is then incubated at 50° C. for a period of 30 minutes and the fluorescence is then measured by irradiation at 330 nm and detection at 390 nm. The presence of hepatitis B RNA in the sample causes the dye crystallite and latex particles to come into close proximity by virtue of the binding of the respective oligonucleotides with the RNA. Upon irradiation of the medium the 9,10-dibromoanthracene is excited and converts ground state oxygen to singlet oxygen. The singlet oxygen reacts with the 7anthene to give a xanthone, which is fluorescent. The fluorescence is measured photometrically and the amount of light over a certain threshold level indicates the presence of hepatitis B RNA in the sample. Irradiation of the medium is conducted at room temperature and the assay is conducted in a homogeneous manner to yield an assay for hepatitis B RNA.

In another embodiment the assay is for the determination of a particular blood group antigen on the surface of a red blood cell, namely, an A group antiget. Latex particles prepared as described above having a particle size of 150–500 nm are utilized. The latex particles have an antibody for the A group antigen covalently linked to the latex particle. The particles also have the photoactive indicator precursor of formula (If):

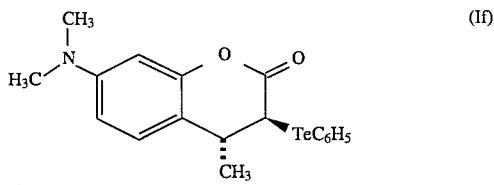

which is dissolved in the latex. This latex particle reagent is combined in the aqueous medium (500 μl) with whole blood (100 μl) and $1\times10^{-4}$M of a photosensitizer, which is a hydrophobic dye of the following formula:

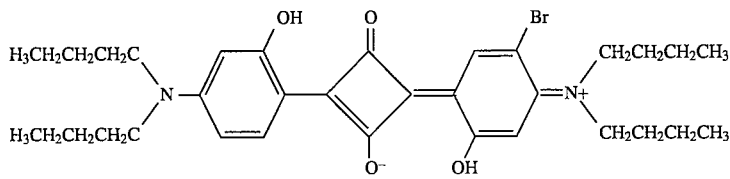

The hydrophobic dye is incorporated into the red cells present in the sample. The medium is incubated at 25° C. for a period of 10 minutes and then irradiated at >650 nm with a tungsten source for a period of 30 seconds. The fluorescence of the solution is then determined by irradiation at 360 nm and detection at 440 nm. The light emitted from the medium is measured and compared to the amount of light obtained in samples known to be free of A group antigen red blood cells. Thus, the amount of light over a threshold level indicates the presence of the A blood group antigen.

The present invention further encompasses compositions comprising a suspendible particle of 25 to 4000 nanometer average diameter comprising a photoactive indicator precursor. The photoactive indicator precursor may be covalently bound to the particle matrix or may be dissolved in the matrix or dissolved in a solvent that is dissolved in the matrix. The particles will preferably be polymeric or be oil droplets or vesicles such as liposomes. Where the particle is a liposome, the photoactive indicator precursor will be associated with the lipid bilayer or dissolved in the aqueous interior of the liposome. The particle will have an sbp member bound to it. Also encompassed are compositions comprised of two complementary sbp members bound to each other wherein one is associated with a photosensitizer and one is associated with a photoactive indicator precursor.

Another aspect of the present invention relates to kits useful for conveniently performing an assay method of the invention for determining the presence or amount of an analyte in a sample suspected of containing the analyte. To enhance the versatility of the subject invention, the reagents can be provided in packaged combination, in the same or separate containers,-so that the ratio of the reagents provides for substantial optimization of the method and assay. The reagents may each be in separate containers or various reagents can be combined in one or more containers depending on the cross-reactivity and stability of the reagents. The kit comprises (1) a composition wherein the composition comprises a suspendible particle comprising a photoactive indicator precursor, the particle having an sbp member bound to it, and (2) a photosensitizer. The photosensitizer can be attached to an sbp member or it can be associated with a particle, to which an sbp member is bound. The kit can further include other separately packaged reagents for conducting an assay including ancillary reagents, and so forth.

Another embodiment of a kit in accordance with the present invention comprises in packaged combination a photoactive indicator precursor associated with a first sbp member and a photosensitizer capable in its excited state of activating oxygen to its singlet state associated with a second sbp member.

EXAMPLES

The invention is demonstrated further by the following illustrative examples. Parts and percentages used herein are by weight unless otherwise specified. Temperatures are in degrees centigrade (°C.). The following abbreviations are used in the Examples:

"Amino-GATTAG"—a modified 42mer oligonucleotide having the sequence shown below:

5' —GATTAG—GATTAG—GATTAG—GATTAG—GATTAG—GATTAG—GATTAG—3' (SEQ ID NO:1)

with the nucleotide (Clontech Laboratories, #5202-1) at the 5'-end substituted as illustrated below:

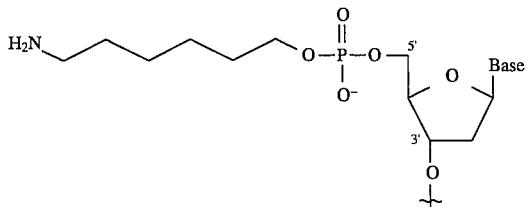

"Biotin-30mer"—a modified 30mer oligonucleotide having the sequence shown below:

5' —CAA—TAC—AGG—TTG—TTG—CCT—TCA—CGC—TCG—AAA—3' (SEQ ID NO:2);

with biotin attached to a modified cytosine (5-methyl-cytosine) at the 5'-end through a linking group as shown below:

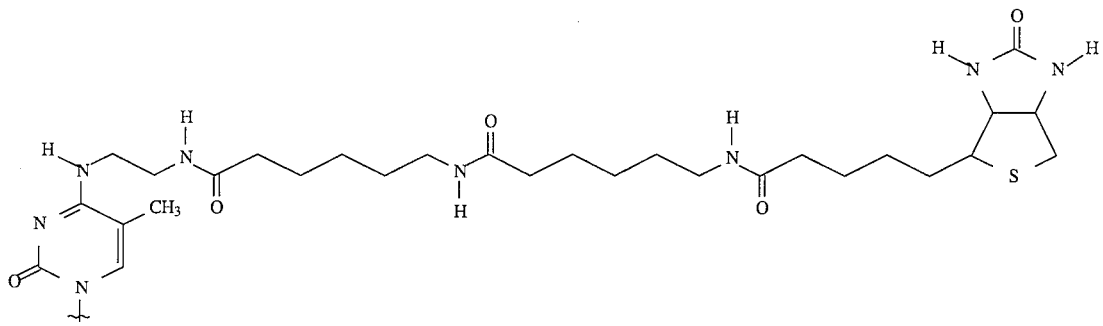

"CTAATC-30mer"—a modified tailed 30mer oligonucleotide having the sequence shown below:

5'-CTG—CCG—GTG—CGC—CAT—GCT—CGC—CCG—CTT—CAC—CTA—ATC—CTA—ATC—CTA—ATC—CTA—ATC—CTA—ATC—CTA—ATC-3' (SEQ ID NO: 3).

"DMF"—dimethyl formamide.

"EDAC"—1-ethyl-3-(3-dimethylaminopropyl)-carbodiimide hydrochloride.

"EDTA"—ethylenediaminetetraacetic acid.

"GATTAG-SH"—a modified 42mer oligonucleotide having the sequence shown below:

5'-GATTAG—GATTAG—GATTAG—GATTAG—GATTAG—GATTAG—GATTAG-3' (SEQ ID NO: 4)

with the 5'-end nucleotide substituted as illustrated below:

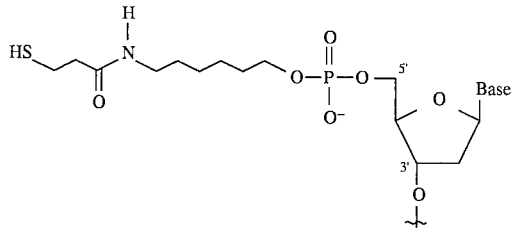

"MES"—2-(N-morpholino)ethane sulfonic acid.
"SPDP"—N-succinimidyl 3-(2-pyridylthio)-propionate.
"Sulfo-SMCC"—4-(N-maleimidomethyl)cyclohexane-1-carboxylate.
"TCEP"—tris-carboxyethyl phosphine.
"THF"—tetrahydrofuran.

Example 1

Preparation of a Photoactive Indicator Precursor

A.

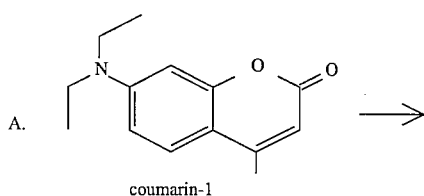

coumarin-1

-continued

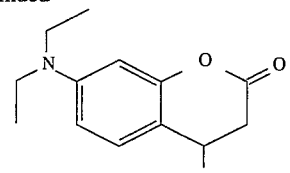

2

A solution of coumarin-1 (11.0 g, 47.5 mmol) in ethyl acetate (150 mL) was treated with 10% Pd/C (100 mg) in a parr bottle. The suspension was then hydrogenated at 80 psi and 80° C. for 6 hours. The suspension was filtered through a bed of celite to remove the Pd/C, and the celite bed washed with warm ethyl acetate (100 mL). The filtrate was concentrated and dried under vacuo to yield 11.0 g (100%) of the 3,4-dihydrocoumarin (2) as an oil;

$^1$H-NMR (CDCl$_3$, 250 MHz): δ7.02 (d,J=8.5 Hz,1H); 6.42 (dd,J=8.5 Hz, 1.7 Hz, 1H); 6.35 (d,J=1.7 Hz, 1H); 4.07 (q,J=7.0 Hz, 4H); 3.06 (m, 1H); 2.80 (dd, J$_{gem}$=15.6 Hz, J$_{vic}$=5.4 Hz, 1H); 2.51 (dd, J$_{gem}$=15.6 Hz, J$_{vic}$=7.7 Hz, 1H); 1.28 (d,J=7.0 Hz, 3H); 1.15 (t,J=7.0 Hz, 6H); MS (EI) calculated for C$_{14}$H$_{19}$NO$_2$, 233: found 233 (M$^+$, 40%); 218 (M$^+$—CH$_3$, 100%).

B.

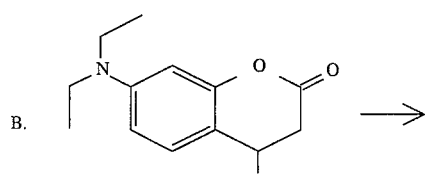

2

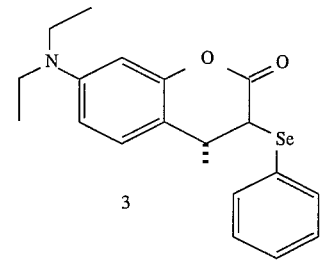

3

A solution of 3,4-dihydrocoumarin 2 (1.68 g, 7.20 mmol) in anhydrous THF (20 mL) was cooled to −78° C. under argon. Lithium diisopropylamide in THF (8.0 mL of 1.0M, 8.0 mmol) was added to the stirred solution and the resultant yellow colored solution was further stirred for 1 hour. Phenyl selenyl chloride (1.50 g, 7.8 mmol) dissolved in THF (10 mL) was subsequently added into the enolate solution. The orange color of the mixture quickly faded to yield a yellow solution. The solution was stirred for 3 hours and quenched with aqueous NH$_4$Cl (10 mL of 1%). After about 10 minutes, dichloromethane (100 mL) was added and the organic phase separated. The aqueous portion was further extracted with CH$_2$Cl$_2$ (2×20 mL) and the organic portions combined. The combined organic portions were washed with brine (20 mL), dried over anhydrous Na$_2$SO$_4$ (25 g) and concentrated to yield 2.10 g of an yellow oil. The oil was purified by chromatography on silica gel with hexane in dichloromethane gradient to yield 1.80 g (67%) of the coumarin-3-phenyl selenide 3, as a white powder. Crystallization from hot hexane afforded 1.30 g of 3 as white needles, m.p. 99°–101° C.;

$^1$H-NMR (C$_6$D$_6$, 250 MHz) δ7.65 (m, 2H); 6.92 (m, 3H); 6.74 (d,J=8.0 Hz, 1H); 6.38 (d,J=1.5 Hz, 1H); 6.25 (dd,J=8.0 Hz, 1.5 Hz, 1H); 3.88 (d,J=2 Hz, 1H); 3.02 (m, 1H); 2.84 (q,J=7.0 Hz, 4H); 0.96 (d,J=7.0 Hz, 3H); 0.80 (t, J=7.0 Hz, 6H); MS (EI) calcd. for C$_{20}$H$_{23}$NO$_2$Se 389; found 389 (M$^+$, 100%); 232 (M$^+$—C$_6$H$_5$Se 70%); 218 (60%); 202 (45%); UV-Vis (toluene) 300 nm (4600); 310 nm (4600); 330 nm (2100).

Example 2

Preparation of a Photoactive Indicator Precursor

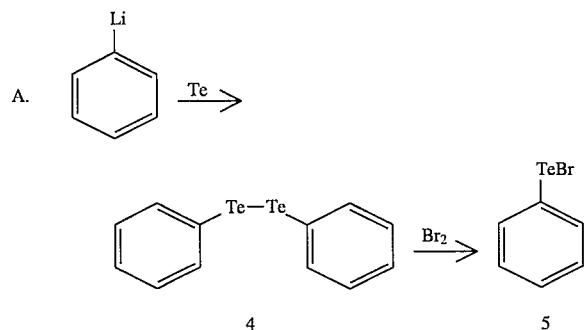

To a stirred suspension of tellurium powder (100 mesh, 13.0 g, 0.10 mol) in dry THF (150 mL) was added a solution of phenyl lithium (60 mL of 1.8M, 0.10 mol) in ether-hexanes. The suspension was stirred at room temperature for 2 hours and then refluxed for 1 hour. The suspension was allowed to cool and water (100 mL) was added followed by overnight stirring. Oxygen gas was bubbled through the suspension for 3 hours. Methylene chloride (200 mL) was added and the organic phase separated. The aqueous phase was further extracted with CH$_2$Cl$_2$ (2×100 mL) and the combined portions washed with brine (100 mL) and dried over anhydrous Na$_2$SO$_4$. The dried solution was passed through a plug of silica (300 g); the filtrate thus obtained was concentrated and crystallized from hot ethanol to yield 13.2 g of the diphenyl ditelluride 4, as orange red needles, m.p. 63–65%C. (lit 63.5°–65° C.); MS (EI) calcd for C$_{12}$H$_{10}$Te$_2$ 414; found 414 (25%); 412 (45%); 410 (50%); 408 (40%); 207 (40%).

The diphenyl ditelluride 4 (1.0 g, 2.5 mmol) was dissolved in TF (10.0 mL) and cooled to 0° C. Bromine (125 μL, 2.5 mmol) in THF (5.0 mL) was added and the solution stirred at 0° C. for 1 hour and allowed to attain room temperature. The reaction mixture was stirred at room temperature until no more starting material was detectable by analytical thin layer chromatography to yield compound 5.

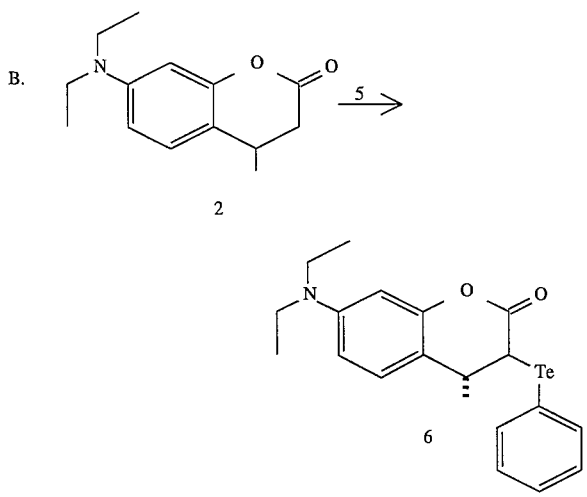

A solution of the 3,4-dihydrocoumarin (240 mg, 1.0 mmol) in anhydrous THF (10 mL) was cooled to −78° C. under argon. Lithium diisopropyl amide (1.1 mL of 1.0M, 1.1 mmol) in THF was added and the solution stirred at −78° C. for 1 hour. A solution of 5 (3 mmol, prepared as described above) in THF was cannulated into the ester enolate and the mixture stirred for 2 hours at −78° C. and then allowed to attain room temperature. The reaction mixture was quenched with aqueous NH$_4$Cl (1%, 5 mL) and stirred for another 5 minutes. The reaction mixture was then extracted with CH$_2$Cl$_2$ (3.25 mL) and the combined organic portions washed with brine (20 mL) and dried over anhydrous Na$_2$SO$_4$ (20 g). Concentration followed by flash chromatography (under subdued lighting) on silica with CH$_2$Cl$_2$ gave 190 mg (43%) of an yellow oil. Crystallization from cyclohexane afforded 165 mg of the coumarin telluride as a light yellow colored solid;

$^1$H-NMR (CDCl$_3$, 250 MHz) δ7.82 (dd,J=7.0 Hz, 1.2 Hz, 2H); 7.31 (m, 1H); 7.26 (m,2H); 6.91 (d,J=8.5 Hz, 1H); 6.38 (dd,J=8.5 Hz, 2.5 Hz, 1H); 6.25 (d,J=2.5 Hz, 1H); 4.05 (d, 2.0 Hz, 1H); 3.33 (q,J=7.0 Hz, 4H); 3.25 (m, 1H); 1.23 (d,J=7.0 Hz, 3H); 1.16 (t,J=7.0 Hz, 6H); MS (EI) calcd. for C$_{20}$H$_{23}$NO$_2$Te 439 (using $^{130}$Te); found 439 (M$^+$., 20%); 232 (M$^+$-C$_6$H$_5$Te, 100%); 217 (25%); 202 (35%); UV-Vis (toluene) 310 nm (3860); 330 nm (2400); 370 nm (510).

Example 3

Preparation of a Photoactive Indicator Precursor

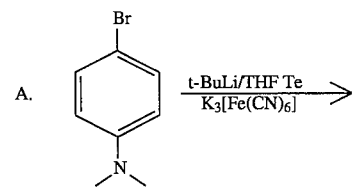

47
-continued

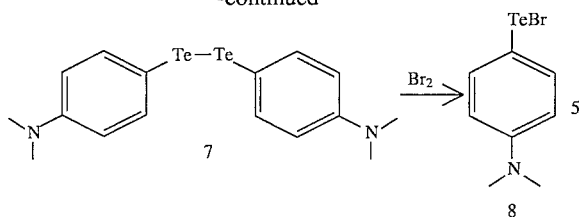

A solution of p-bromo-N,N-dimethyl aniline (10.0 g, 50.0 mmol) in anhydrous TF (200 mL) was cooled to −78° C. under argon. Into this cooled solution was carefully added t-butyl lithium (56 mL of 1.8M, 100 mmol) in pentane, and the resulting yellow suspension stirred for 1 hour at −78° C. Finely ground tellurium powder (6.50 g, 50 mmol) was added under a stream of argon. The reaction mixture was then allowed to attain room temperature, by that time (~2 hours) most of the tellurium had dissolved. The reaction mixture was quenched with water (20 mL) and poured into aqueous $K_3[Fe(CN)_6]$ solution (17 g in 200 mL, 0.052 mol). The mixture was stirred for 1 hour and then extracted with $CH_2Cl_2$ (3×200 mL). The combined organic portions were washed with brine (100 mL) and dried over anhydrous $Na_2SO_4$ (100 g). The dried material was passed through a plug of silica (300 g) and the filtrate concentrated to yield 12.2 g of an orange-red paste. Crystallization from ethanol gave 8.6 g of the ditelluride 7, as an orange red powder. Another batch (2.2 g) was recovered from the mother liquor; MS (EI) calculated for $C_{16}H_{20}N_2Te_2$, 500; found 500 (20%); 498 (40%); 496 (45%); 250 (100%); 240 (98%).

The ditelluride 7 (1.70 g, 3.4 mmol) was dissolved in a minimum amount of anhydrous THF and cooled to 0° C. The solution was treated with bromine (175 µL, 3.4 mmol) and the mixture stirred at 0° C. for 3 hours to yield a solution containing the desired product.

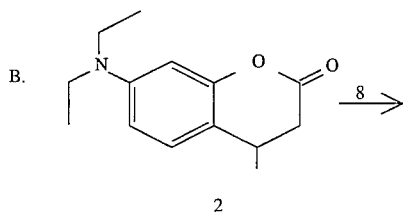

The product 8 was then cannulated under argon into a solution of the dihydro coumarin 2 (800 mg, 3.4 mmol) and lithium diisopropyl amide (3.5 mL of 1.0M, 3.5 mmol) in THF. The resulting orange red mixture was allowed to attain room temperature and quenched with aqueous $NH_4Cl$ (10 mL of 1.0%). The mixture was subsequently extracted with $CH_2Cl_2$ (3×50 mL) and the pooled organic portion dried with brine (50 mL) and anhydrous $Na_2SO_4$. Concentration

48 followed by flash chromatography (under subdued light) on silica with $CH_2Cl_2$ gave 510 mg of the coumarin 3-(4-dimethylamino)phenyl telluride 9, together with 110 mg of the starting dihydro coumarin 2. The yield of 9 was 37% based upon recovered starting material;

$^1$H-NMR (CDCl$_3$, 250 MHz) δ7.65 (d,J=8.0 Hz, 2H); 6.92 (d,J=8.5 Hz, 1H); 6.52 (d,J=8.0 Hz, 2H); 6.41 (dd,J=8.5 Hz, 1.5 Hz, 1H); 6.24 (d,J=1.5 Hz, 1H); 4.03 (d, 2 Hz, 1H); 3.38 (q,J=7.0 Hz, 4H); 3.25 (m,H); 2.95 (s,6H); 1.19 (d,J= 7.0 Hz, 3H); 1.14 (t,J=7.0 Hz, 6H).; MS (EI) calcd. for $C_{22}H_{28}N_2O_2Te$, 482 (using $^{130}$Te); found 482 (M$^+$., 20%); 252 (20%); 232 (M$^+$—$C_8H_{10}$Te, 100%); UV-Vis (toluene) 300 nm (18000); 320 nm (13600); 330 nm (8400).

Example 4

Preparation of Photoactive Indicator Precursor Particles (Acceptor Beads)

A 0.3M solution of coumarin-3-(4-dimethylamino)phenyl telluride 9 was prepared in degassed ethoxy ethanol by gentle warming. Ethylene glycol (1 mL) was heated to 105°–110° C. in a 4 mL vial. A stock latex suspension (200 µL of 10% solids in $H_2O$) was added to the vial and the mixture stirred magnetically under argon. Comarin-3-(4-dimethylamino)phenyl telluride 9 (200 µL, 0.3M in ethoxy-ethanol) was added slowly to the mixture and the resulting mixture stirred for 5 minutes, then allowed to attain room temperature under argon. After cooling, the suspeneion was treated with ethanol (3 mL) and transferred to a centrifuge tube. The mixture was then centrifuged at 15,000 rpm (Sorval, SA 600 rotor) for 1 hour. The supernatant was carefully decanted and the pellet resuspended in aqueous ethanol (4.0 mL) by sonication. The suspension was centrifuged at 15,000 rpm for 1 hour. The supernatant was once again removed and the pellet was resuspended in water (4 mL). Following a final centrifugation and removal of supernatant, the pellet was resuspended in water to a final volume of 2 mL to a yield of 10 mg/mL photoactive indicator precursor particles suspension.

Example 5

Preparation of Streptavidin-Photoactive Indicator Precursor Dyed Particles

The photoactive indicator precursor particles (1 mL of 10 mg/mL) suspension prepared in Example 4 above was added to an EDAC solution (0.5 mg/mL, 1 mL of 0.02M phosphate buffer, pH 6.0) cooled to 0° C. The suspension was stirred under argon for 30 minutes. After this time, the suspension was added dropwise into a streptavidin solution (5 mg/mL, 1 mL) in borate buffer (0.2M, pH 9.0) kept at ~0° C. The suspension was stirred for 1 hour and allowed to warmup to room temperature. Water (1 mL) was added and the mixture centrifuged at 15,000 rpm for 1 hour. The supernatant was discarded and the pellet suspended in water (4 mL) by sonication. The sample was recentrifuged in water (4 mL) by sonication, and after a final centrifugation at 15,000 rpm for 30 minutes, the resultant pellet was suspended in water (5 mL). This gave a 2 mg/mL suspension of streptavidin-photoactive indicator precursor particles. The presence of streptavidin was confirmed by $^3$H biotin binding and quantitated to 2500±250 streptavidin/particle.

Example 6

Preparation of Maleimidated Dextran Photosensitizer Particles

A. Staining of particles.

A dye mixture of chlorophyll-a (2.0 mM) and tetrabutyl squarate (4.0 mM) in benzyl alcohol was prepared. Ethylene glycol (80 mL) was placed in a 125 mL Erlenmeyer flask and warmed to 125° C. on a laboratory hot plate. The dye mixture in benzyl alcohol (8 mL) was then added followed immediately by stock latex suspension (10 mL of 10% solids). Heating was discontinued and the flask and its contents allowed to attain room temperature. After cooling, the mixture was diluted with an equal volume of ethanol and immediately centrifuged at 15,000 rpm for two hours. The bluish-green supernatant was discarded and the pellet suspended in 50 mL of ethanol by sonication. The suspension was centrifuged at 15,000 rpm for one hour and the faintly blue supernatant decanted. The pellet was resuspended in 50% aqueous ethanol (50 mL) by sonication to disperse the particles. Centrifugation was repeated at 15,000 rpm for an hour. The supernatant was decanted and the pellet resuspended in water by sonication. Following a final centrifugation, the pellets were resuspended in water to a final volume of 20 mL.

B. Preparation of Maleimidated Dextran Photosensitizer Particles.

Aminodextran (500 mg) was partially maleimidated by reacting it with sulfo-SMCC (157 mg, 10 mL $H_2O$). The sulf-SMCC was added to a solution of the aminodextran (in 40 mL, 0.05M $Na_2HPO_4$, pH 7.5) and the resulting mixture was incubated for 1.5 hr. The reaction mixture was then dialyzed against MES/NaCl (2×2L, 10 mM MES, 10 mM NaCl, pH 6.0, 4° C.). The maleimidated dextran was centrifuged at 15,000 rpm for 15 minutes and the supernatant collected. The supernatant dextran solution (54 mL) was then treated with imidazole (7 mL of 1.0M solution) in MES buffer (pH 6.0) and into this stirred solution was added the stained photosensitizer particles (10 mL of 10mg/mL). After stirring for 10 minutes the suspension was treated with EDAC (7 mmol in 10 mM pH 6.0 MES) and the suspension stirred for 30 minutes. After this time, SurfactAmps® (Pierce) Tween-20 (10%, 0.780 mL) was added to the reaction mixture for a final concentration of 0.1%. The particles were then centrifuged at 15,000 rpm for 45 minutes and the supernatant discarded. The pellet was resuspended in MES/NaCl (pH 6.0, 10 mM, 100 mL) by sonication. Centrifugation at 15,000 rpm for 45 minutes, followed by pellet resuspension after discarding the supernatant, was performed twice. The maleimidated dextran photosensitizer particles were stored in water as a 10 mg/mL suspension.

Example 7

Preparation of GATTAG-Photosensitizer Particles.

Amino-GATTAG (180 µL, 50 mmol) (prepared as described below in Example 8) in water was treated with 0.25M borax (50 µL) to give a pH of 9.2. SPDP (50 mg/mL in dry DMF) was added in four aliquots at 0, 10, 20 and 30 minutes (33.8 µmol total). The reaction mixture was allowed to stand for 2 hours. Ice cold ethanol (2.1 mL) was added and the product left in the freezer overnight. The cloudy product mixture was split into two Eppendorf tubes and centrifuged at maximum speed for 10 minutes. The supernatant was carefully removed and the pellet dissolved in 400 µL $H_2O$. Into this solution was added 2.5 M acetate buffer (20 µL, 2.5M, pH 5.3).

TCEP in distilled water (10 µL, 20 mM) was added and the reduction allowed to proceed for 30 minutes at room temperature. Absolute ethanol (1.2 mL) was added and the reaction mixture put in the freezer for 2 hours. The reaction mixture was centrifuged at full speed in the cold room and the precipitated GATTAG-SH oligonucleotide was removed as a pellet. The pellet was dissolved in 200 µL of 50 mM $Na_2HPO_4$ buffer (pH 6.85) containing 20 mM EDTA. The solution was degassed and kept under argon. This solution was then added to the maleimidated dextran photosensitizer particles (14.2 mg/1.5 mL) (prepared above in Example 6) and the reaction mixture allowed to stand overnight. The mixture was centrifuged at 15,000 rpm for 1 hour and the supernatant discarded. The pellet was resuspended in water (2 mL) and centrifuged at 15,000 rpm for 1 hour. The supernatant was discarded and the pellet resuspended in water (2 mL). After a final centrifugation the GATTAG-photosensitizer particles were stored in 2 mL of water solution as a suspension.

Example 8

Assay for Detecting DNA

A. The target 65mer oligonucleotide with the sequence shown below:

5'-GTG—AAG—CGG—GCG—AGC—ATG—GCG—
CAC—CGG—CAG—AGC—ATT—TTC—GAG—CGT—
GAA—GGC—AAC—AAC—CTG—TAT—TG-3' (SEQ ID NO: 5);

and CTAATC-30mer and amino-CATTAG were prepared on a Milliget Biosearch DNA synthesizer (Model #8750) using standard solid phase phosphoramidite methodology (see *Oligonucleotide Syntheses—A Practical Approach* (1984), Gait M. J., Ed., IRL Press Oxford.) The protocol briefly consisted of (a) removal with dichloroactic acid of the 5'-dimethoxytrityl group on the nucleoside attached to the solid support; (b) coupling of the incoming nucleoside, which contains a 5'-hydroxyl protecting group (preferably dimethoxytrityl) and a 3'-hydroxyl protecting group (preferably N, N-diisopropylphosphoramidite), using tetrazole as the catalyst; (c) a capping step with acetic anhydride; and (d) iodine oxidation to convert the phosphite triester into a phosphate triester. At the conclusion of the synthesis ammonium hydroxide was used to (a) cleave the synthesized polynucleotide from the support; (b) remove the phosphoryl protecting groups (β-cyanoethyl); and (c) to remove the base protecting groups. The oligonucleotide was finally purified by HPLC. B. Biotin-30mer was prepared similarly as above except that the base of the last incoming nucleotide was a 5-methylcytosine with a protected amine-modifier (American Bionetics, #ABN2599) as shown below:

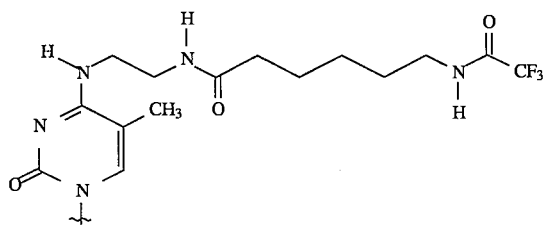

After deprotection, the free amine was reacted with biotin-LC-NHS (Pierce, #21335G) at a 1:60 molar ratio of the two reagents in 0.1M $NaHCO_3$, pH 9.0. Following incubation overnight at room temp, the resulting oligonucleotide was analyzed and purified on a 12% denaturing polyacrylamide gel. C. The assay was performed by mixing various volumes (0–80L of 21 nM) of target 65mer oligonucleotide with CTAATC-30mer (200L of 15 nM) and biotin-30mer (200 µL of 15 nM) in TRIS/EDTA/NaCl solution (pH 8.0, 100 mM, 0.1 mM, 0.30M, respectively) contained in a 1.5 mL Eppendorf tube. The volumes were made up to 0.5 mL and the solution annealed at 55° C. for 30 minutes so that the 30mer probes could hybridize with their complements on the target 65mer oligonucleotide upon cooling. The reaction mixture was cooled to room temperature and then treated with the streptavidin-photoactive indicator precursor particles (100 µL of 100 µg/mL) followed by GATTAG-photosensitizer particles (400 µL of 100 µg/mL).

The mixture was gently vortexed and allowed to incubate for 2 hours at room temperature. The suspension was then transferred to a 12×75 mm test tube and irradiated for 5 minutes with a Dolan-Jenner lamp (tungsten) equipped with a 610 nm cutoff filter. The sample was treated with an equal volume (1 mL) of buffer and transferred to a fluorometer. The fluorescence units corresponding to an excitation with a 360 NB filter and 420 NB filter emission were recorded. The resulting standard curves for two individual assays are shown in FIG. 1.

Although the foregoing invention has been described in some detail by way of illustration and example for purposes of clarity and understanding, it will be obvious that certain changes or modifications may be practiced within the scope of the appended claims.

What is claimed is:

1. A compound of the following formula:

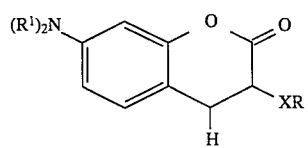

wherein

R is an organic or organometallic group bound to X through an unsaturated carbon atom, a silicon atom, or a tin atom; and $R^1$ is hydrogen or alkyl; and X is selenium or tellurium; and wherein the remaining hydrogen atom on the carbon adjacent to the carbon to which XR is bound may be replaced by alkyl or alkylene substituents.

2. The compound of claim 1 which is selected from the group consisting of the following compounds:

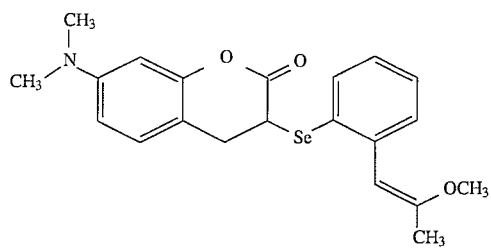
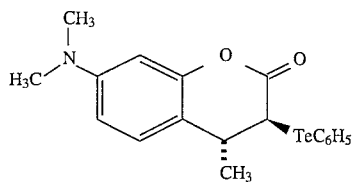
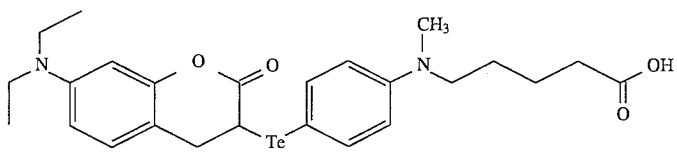
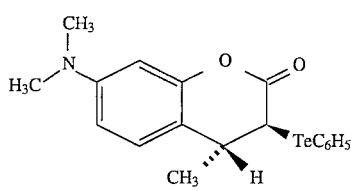
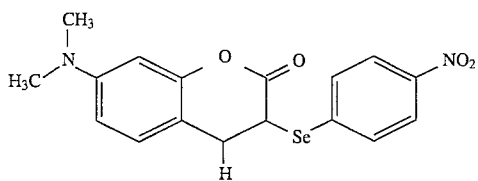
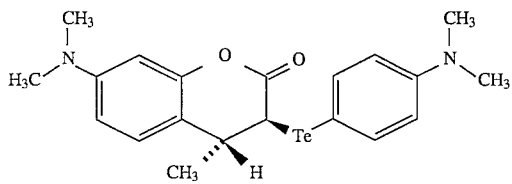
3. A compound of the formula:
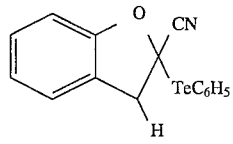
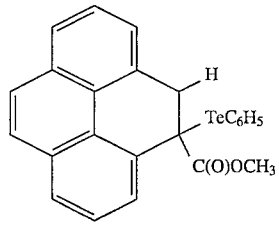
-continued
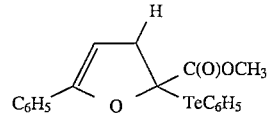
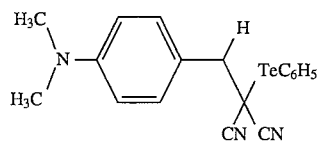
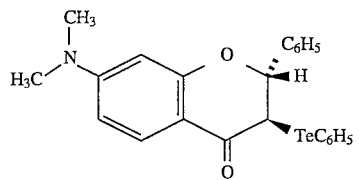

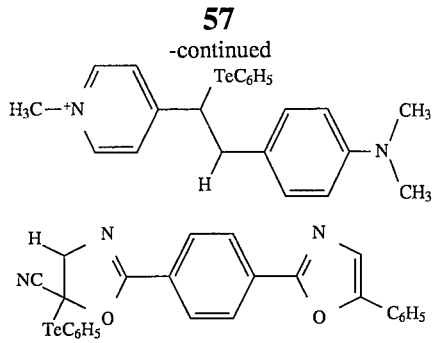

4. A method for preparing a photoactive indicator, which method comprises reacting a compound of the structure:

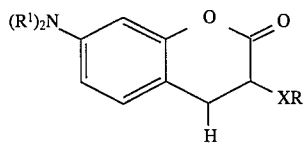

wherein

H is cis to the XR group;

X is a selenium or tellurium;

R is an organic or organometallic group bound to X through an unsaturated carbon atom, a silicon atom, or a tin atom; and A, when taken with the carbon-carbon group, forms an alicyclic ring optionally fused to one or more aromatic rings or a heterocyclic ring;

with singlet oxygen to yield a photoactive indicator having an extinction coefficient of at least 10,000 $M^{-1}cm^{-1}$ at its absorption maximum and a fluorescence emission quantum yield of at least 0.1.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: synthetic ( x i ) SEQUENCE DESCRIPTION: SEQ ID NO:1:

```
GATTAGGATT AGGATTAGGA TTAGGATTAG GATTAGGATT AG                    42
```

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: synthetic ( x i ) SEQUENCE DESCRIPTION: SEQ ID NO:2:

```
CAATACAGGT TGTTGCCTTC ACGCTCGAAA                                  30
```

( 2 ) INFORMATION FOR SEQ ID NO:3:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( i i ) MOLECULE TYPE: DNA (genomic)

(iii) HYPOTHETICAL: NO (iv) ANTI-SENSE: NO (vi) ORIGINAL SOURCE:
 (A) ORGANISM: synthetic (xi) SEQUENCE DESCRIPTION: SEQ ID NO:3:

CTGCCGGTGC GCCATGCTCG CCCGCTTCAC CTAATCCTAA TCCTAATCCT AATCCTAATC    60

CTAATC    66

(2) INFORMATION FOR SEQ ID NO:4:

(i) SEQUENCE CHARACTERISTICS:
 (A) LENGTH: 42 base pairs
 (B) TYPE: nucleic acid
 (C) STRANDEDNESS: single
 (D) TOPOLOGY: linear (ii) MOLECULE TYPE: DNA (genomic)

(iii) HYPOTHETICAL: NO (iv) ANTI-SENSE: NO (vi) ORIGINAL SOURCE:
 (A) ORGANISM: synthetic (xi) SEQUENCE DESCRIPTION: SEQ ID NO:4:

GATTAGGATT AGGATTAGGA TTAGGATTAG GATTAGGATT AG    42

(2) INFORMATION FOR SEQ ID NO:5:

(i) SEQUENCE CHARACTERISTICS:
 (A) LENGTH: 65 base pairs
 (B) TYPE: nucleic acid
 (C) STRANDEDNESS: single
 (D) TOPOLOGY: linear (ii) MOLECULE TYPE: DNA (genomic)

(iii) HYPOTHETICAL: NO (iv) ANTI-SENSE: NO (vi) ORIGINAL SOURCE:
 (A) ORGANISM: synthetic (xi) SEQUENCE DESCRIPTION: SEQ ID NO:5:

GTGAAGCGGG CGAGCATGGC GCACCGGCAG AGCATTTTCG AGCGTGAAGG CAACAACCTG    60

TATTG    65